United States Patent
Ramos et al.

(10) Patent No.: US 12,337,164 B2
(45) Date of Patent: *Jun. 24, 2025

(54) HVAD FLOW PULSATILITY TRACKER

(71) Applicant: HeartWare, Inc., Miami Lakes, FL (US)

(72) Inventors: Veronica Ramos, Homestead, FL (US); Neethu Lekshmi Vasudevan Jalaja, Miami, FL (US); Michael Brown, Dresher, PA (US)

(73) Assignee: HeartWare, Inc., Miami Lakes, FL (US)

( * ) Notice: Subject to any disclaimer, the term of this patent is extended or adjusted under 35 U.S.C. 154(b) by 948 days.

This patent is subject to a terminal disclaimer.

(21) Appl. No.: 17/405,553

(22) Filed: Aug. 18, 2021

(65) Prior Publication Data

US 2021/0379361 A1 Dec. 9, 2021

Related U.S. Application Data

(63) Continuation-in-part of application No. 16/809,731, filed on Mar. 5, 2020, now Pat. No. 11,413,445.

(60) Provisional application No. 62/816,957, filed on Mar. 12, 2019.

(51) Int. Cl.
*A61M 60/546* (2021.01)
*A61M 60/178* (2021.01)
(Continued)

(52) U.S. Cl.
CPC ........ *A61M 60/546* (2021.01); *A61M 60/178* (2021.01); *A61M 60/232* (2021.01);
(Continued)

(58) Field of Classification Search
CPC ...... A61M 2205/18; A61M 2205/3334; A61M 2205/50; A61M 60/148; A61M 60/178;
(Continued)

(56) References Cited

U.S. PATENT DOCUMENTS

| 5,888,242 A | 3/1999 | Antaki et al. |
| 6,991,595 B2 | 1/2006 | Burke et al. |
| (Continued) | | |

FOREIGN PATENT DOCUMENTS

| CN | 104321089 A | 11/2016 |
| WO | 2014049458 A1 | 4/2014 |
| (Continued) | | |

OTHER PUBLICATIONS

International Search Report and Written Opinion dated Oct. 9, 2020, for corresponding International Application No. PCT/US2020/021322; International Filing Date: Mar. 6, 2020 consisting of 19 pages.

(Continued)

*Primary Examiner* — Jon C Morales
(74) *Attorney, Agent, or Firm* — Shumaker & Sieffert, P.A.

(57) ABSTRACT

A method of predicting an adverse event in a patient having an implantable blood pump including correlating a pulsatility value to a flow trough value associated with the blood pump to determine a flow peak value; dividing the determined flow peak value by a pump current to determine a pulsatility peak value; tracking a first moving average of the pulsatility peak value, the first moving average defining a threshold range; tracking a second moving average of the pulsatility peak value, the second moving average being faster than the first moving average; and generating an alert when the second moving average deviates from the threshold range.

20 Claims, 22 Drawing Sheets

(51) Int. Cl.
*A61M 60/232* (2021.01)
*G05B 23/02* (2006.01)
*G16H 40/67* (2018.01)
*G16H 50/30* (2018.01)
*G16H 50/70* (2018.01)
*G16H 10/60* (2018.01)

(52) U.S. Cl.
CPC ........... *G05B 23/027* (2013.01); *G16H 40/67* (2018.01); *G16H 50/30* (2018.01); *G16H 50/70* (2018.01); *A61M 2205/18* (2013.01); *A61M 2205/702* (2013.01); *G16H 10/60* (2018.01)

(58) Field of Classification Search
CPC .. A61M 60/216; A61M 60/422; A61M 60/50; A61M 60/515; A61M 60/523; A61M 60/562; A61M 60/592; A61M 60/17; A61M 60/546
See application file for complete search history.

(56) References Cited

U.S. PATENT DOCUMENTS

| | | | |
|---|---|---|---|
| 7,175,588 B2 | 2/2007 | Morello | |
| 7,645,225 B2 | 1/2010 | Medvedev et al. | |
| 8,897,873 B2 | 11/2014 | Schima et al. | |
| 8,961,390 B2 | 2/2015 | LaRose et al. | |
| 9,511,179 B2 | 12/2016 | Casas et al. | |
| 9,623,161 B2 | 4/2017 | Medvedev et al. | |
| 9,795,726 B2 | 10/2017 | Brown et al. | |
| 11,413,445 B2 * | 8/2022 | Brown | A61M 60/422 |
| 2003/0199727 A1 | 10/2003 | Burke | |
| 2012/0035490 A1 | 2/2012 | Shen | |
| 2014/0100413 A1 | 4/2014 | Casas et al. | |
| 2017/0224895 A1 | 8/2017 | Voskoboynikov et al. | |
| 2020/0289730 A1 | 9/2020 | Brown et al. | |
| 2020/0405931 A1 | 12/2020 | Reyes et al. | |

FOREIGN PATENT DOCUMENTS

| | | |
|---|---|---|
| WO | 2015195916 A1 | 12/2015 |
| WO | 2018227156 A | 12/2018 |
| WO | 2019013794 A1 | 1/2019 |

OTHER PUBLICATIONS

Notice of Allowance from U.S. Appl. No. 16/809,731, dated Apr. 29, 2022, 7 pp.

Response to Office Action mailed Jan. 20, 2022, from U.S. Appl. No. 16/809,731, filed Apr. 13, 2022, 9 pp.

Office Action from U.S. Appl. No. 16/809,731, dated Jan. 20, 2022, 7 pp.

* cited by examiner $$\frac{100 \cdot (\text{Average}(\text{Pulsatility}))^3}{(\text{Average}(\text{Trough}) + 2500)^2 \cdot \text{Average}(\text{Flow MLPM}) \cdot \text{StandardDeviation}(\text{Trough})}$$

HVAD FLOW PULSATILITY TRACKER

CROSS-REFERENCE TO RELATED APPLICATION

This application is a Continuation-In-Part of U.S. application Ser. No. 16/809,731, filed Mar. 5, 2020 and claims the benefit of U.S. Application Ser. No. 62/816,957, filed Mar. 12, 2019.

FIELD

The present technology is generally related to an implantable blood pump.

BACKGROUND

Mechanical circulatory support devices, such as implantable blood pumps, are used to assist the pumping action of a failing heart. Such blood pumps may include a housing with an inlet, an outlet, and a rotor mounted within the housing. The inlet may be connected to a chamber of a patient's heart, for example the left ventricle, using an inflow cannula. The outlet may be connected to an artery, such as the aorta. Rotation of the rotor drives blood from the inlet towards the outlet and thus assists blood flow from the chamber of the heart into the artery.

Known blood pumps are susceptible to experiencing adverse events which may result in costly hospitalizations and medical interventions for patients. For example, whether systemic or cardio-pulmonary in nature, adverse events can impact ventricular volume and pressure which is reflected in pump parameters such as power, flow, current, speed, and/or derivatives of pump parameters, such as a patient's circadian cycle, heart rate, aortic valve status, and suction burden. Pump parameters obtained in real time may indicate an adverse event, but do not provide an analysis of changes in pump parameters over time which may be useful in identifying changes in a patient's health condition.

SUMMARY

The techniques of this disclosure generally relate to analyzing health conditions of patients having an implantable blood pump and providing an alert associated with negative health conditions.

In one aspect, the present disclosure provides a method of predicting an adverse event in a patient having an implantable blood pump including correlating a pulsatility value to a flow trough value associated with the blood pump to determine a flow peak value; dividing the determined flow peak value by a pump current to determine a pulsatility peak value; tracking a first moving average of the pulsatility peak value, the first moving average defining a threshold range; tracking a second moving average of the pulsatility peak value, the second moving average being faster than the first moving average; and generating an alert when the second moving average deviates from the threshold range.

In another aspect, the disclosure provides recording a plurality of alert occurrences over a time period, and based on the plurality of alert occurrences, determining a risk factor associated with a predicted onset of the adverse event.

In another aspect, the disclosure provides based on the determined risk factor, automatically classifying a patient's physiological state among a ranking system.

In another aspect, the disclosure provides determining a standard deviation of the first moving average, the first moving average and the standard deviation defining the threshold range.

In another aspect, the disclosure provides the first moving average being a twenty-four-hour moving average and the second moving average being approximately a two-hour duration.

In one aspect, the present disclosure provides a system of predicting an adverse event in a patient having an implantable blood pump including the blood pump and a processor in communication with the blood pump, the processor having process circuitry configured to correlate a pulsatility value to a flow trough value associated with the blood pump to determine a flow peak value; divide the determined flow peak value by a pump current to determine a pulsatility peak value; track a first moving average of the pulsatility peak value, the first moving average defining a threshold range; track a second moving average of the pulsatility peak value, the second moving average being faster than the first moving average; and generate an alert when the second moving average deviates from the threshold range.

In another aspect, the disclosure provides the system including the process circuitry being configured to record a plurality of alert occurrences over a time period, and based on the plurality of alert occurrences, determine a risk factor associated with a predicted onset of the adverse event.

In one aspect, the present disclosure provides a method of predicting an adverse event in a patient having an implantable blood pump including tracking an average pulsatility value associated with the blood pump; tracking a plurality of parameters associated with the blood pump including an average flow trough value, an average flow value, and a standard flow trough deviation value, the standard flow trough deviation value being measured with respect to the average flow trough value; correlating the average pulsatility value to the plurality of parameters; determining an adverse event index value using the correlated average pulsatility value relative to the plurality of parameters; comparing the adverse event index value to a predetermined threshold range; and generating an alert when the compared adverse event index value deviates from the predetermined threshold range.

In another aspect, the disclosure provides correlating the average pulsatility value to a scaling coefficient.

In another aspect, the disclosure provides correlating the standard flow trough deviation value to an offset value.

In another aspect, the disclosure provides determining a plurality of adverse event index values during a plurality of time periods, comparing the plurality of adverse event index values to each other, and based on the compared plurality of adverse event index values, classifying a patient's physiological state among a ranking system.

In another aspect, the disclosure provides the average pulsatility value and the plurality of parameters associated with the blood pump being expressed as a waveform, and the adverse event index value exceeding the predetermined threshold range is expressed as an abnormal feature of the waveform.

In one aspect, the present disclosure provides a system of predicting an adverse event in a patient having an implantable blood pump including the blood pump; and a processor in communication with the blood pump, the processor having process circuitry configured to track an average pulsatility value associated with the blood pump; track a plurality of parameters associated with the blood pump including an average flow trough value, an average flow value, and a standard flow trough deviation value, the standard flow trough deviation value being measured with respect to the average flow trough value; correlate the average pulsatility value to the plurality of parameters; determine an adverse event index value using the correlated average pulsatility value relative to the plurality of parameters; compare the adverse event index value to a predetermined threshold range; and generate an alert when the compared adverse event index value deviates from the predetermined threshold range.

In one aspect, the present disclosure provides a method of predicting an adverse event in a patient having an implantable blood pump including identifying a flow trough value associated with the blood pump during use; comparing the flow trough value to a standard deviation flow value and an average flow value; determining a flow trough index value using the compared flow trough value to the standard deviation flow value and the average flow value; and generating an alert when the flow trough index value deviates from a predetermined threshold range.

In another aspect, the disclosure provides the based on the determined flow trough index value, quantifying a suction prevalence associated with the blood pump.

In another aspect, the disclosure provides determining a plurality of flow trough index values, and based on the determined plurality of flow trough index values, quantifying a suction prevalence associated with the blood pump.

In another aspect, the disclosure provides the based on the suction prevalence, classifying a patient's physiological state among a ranking system.

In another aspect, the disclosure provides the determining a presence of a negative flow trough value relative to a flow scale, if the negative flow trough value is present, correlating the flow trough value to a constant, and following the correlated flow trough value to the constant, determining the flow trough index value.

In another aspect, the disclosure provides multiplying the flow trough index value by a corrective factor.

In another aspect, the disclosure provides the dividing the standard deviation flow value and the average flow value.

In one aspect, the present disclosure provides a system of predicting an adverse event in a patient having an implantable blood pump including the blood pump; and a processor in communication with the blood pump, the processor having process circuitry configured to identify a flow trough value associated with the blood pump during use; compare the flow trough value to a standard deviation flow value and an average flow value; determine a flow trough index value using the compared flow trough value to the standard deviation flow value and the average flow value; and generate an alert when the flow trough index value deviates from a predetermined threshold range.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
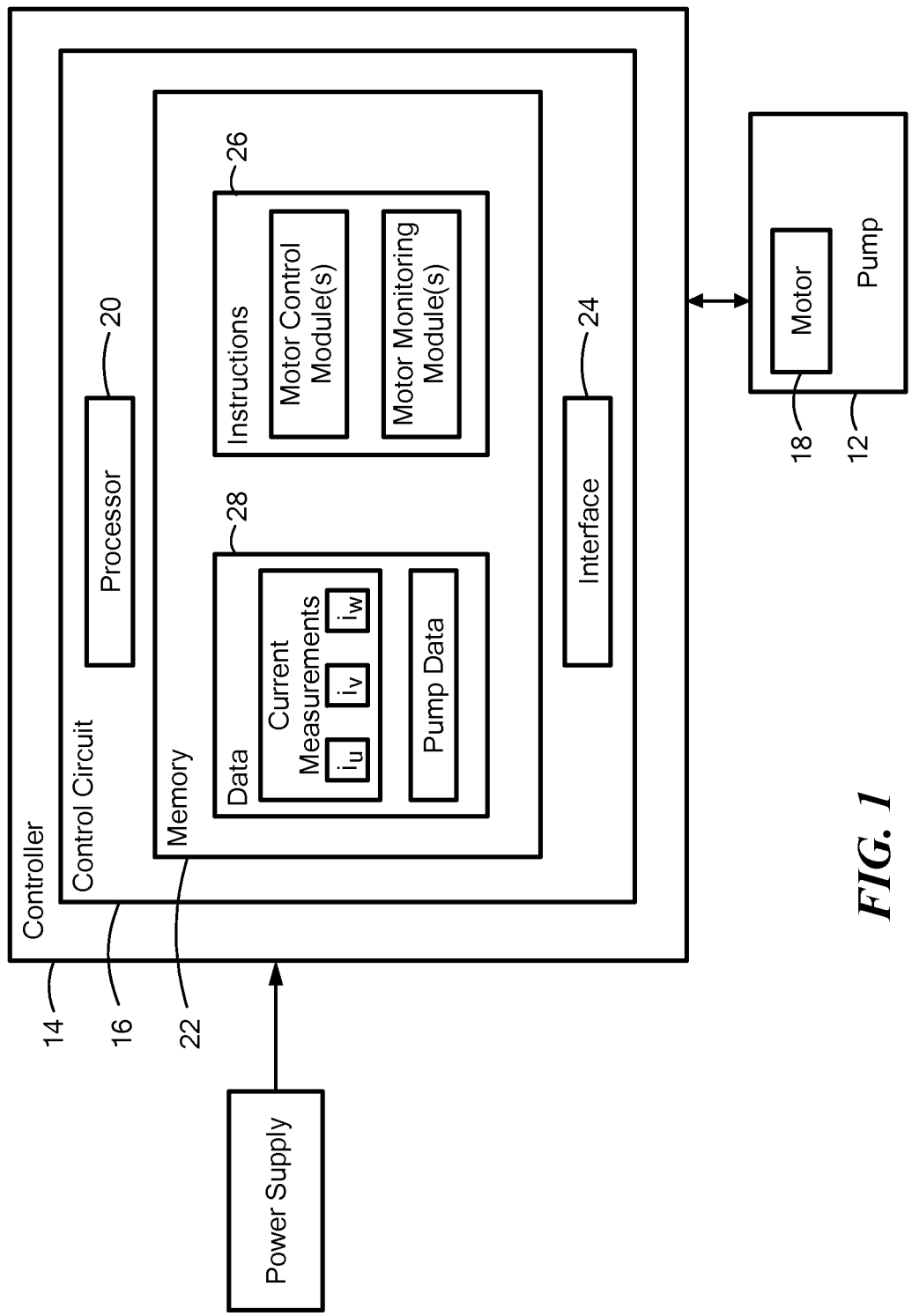
FIG. 1 is a block diagram that illustrates a system including a processor and an implantable blood pump.

Before describing in detail exemplary embodiments, it is noted that the embodiments reside primarily in combinations of system components and processing steps related to an implantable blood pump. Accordingly, the system and process components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Referring now to the drawings in which like reference designators refer to like elements, there is shown an exemplary system constructed in accordance with the principles of the present disclosure and designated generally as "10." The system, and corresponding methods, provide a retrospective analysis of one or more blood pump parameters obtained during operation of the blood pump. Information gained from the analysis may be used to determine a patient's health condition, including whether the patient's condition is worsening over time. The system 10 may generate an alert when the patient's condition deviates from a predetermined threshold which may indicate one or more worsening conditions.

FIG. 1 is a block diagram of the system 10 including an implantable blood pump 12 in communication with a controller 14. The blood pump 12 may be the HVAD® Pump or another mechanical circulatory support device fully or partially implanted within the patient and having a movable element, such as a rotor, configured to pump blood from the heart to the rest of the body. The controller 14 includes a control circuit 16 for monitoring and controlling startup and subsequent operation of a motor 18 implanted within the blood pump 12. The controller 14 may also include a processor 20, a memory 22, and an interface 24. The memory 22 is configured to store information accessible by the processor 20 including instructions 26 executable by the processor 20 and/or data 28 that may be retrieved, manipulated, and/or stored by the processor 20. In particular, the processor 20 includes circuitry configured to carry out the steps discussed herein with respect to the methods. As such, reference to the system 10 executing steps of the methods is intended to include the processor 20.

In one example, the information stored by the processor 20 includes blood pump parameters determined by the system 10, such as an estimated amount of blood flow through the blood pump 12, a flow trough value, and a flow pulsatility value. The amount of blood flow through the blood pump 12 is computed in liters per minute, or another measuring unit, from the pump speed, the patient's hematocrit, and the pump current. For example, when the blood pump 12 is operating, the parameters are captured during a select timeframe, such as a sliding two-second window, of an estimated flow waveform and stored as log files. The minimum and the maximum flow values are observed during the two-second window. The flow trough value is the minimum flow value and the flow peak value is the maximum flow value. The flow pulsatility value i.e., pulsatility value, is the difference between the minimum and the maximum flow values. The flow pulsatility may be impacted by the patient's conditions, for example, left ventricular contractility, right heart function, and left ventricular afterload. The timeframe may vary and the exemplary timeframe of two-seconds is provided in order to capture at least one full cardiac cycle while accounting for a patient's heart rate as low as 30 BPM. The same process may be used to determine the parameters using real-time waveforms rather than the log files.

Figure 2:
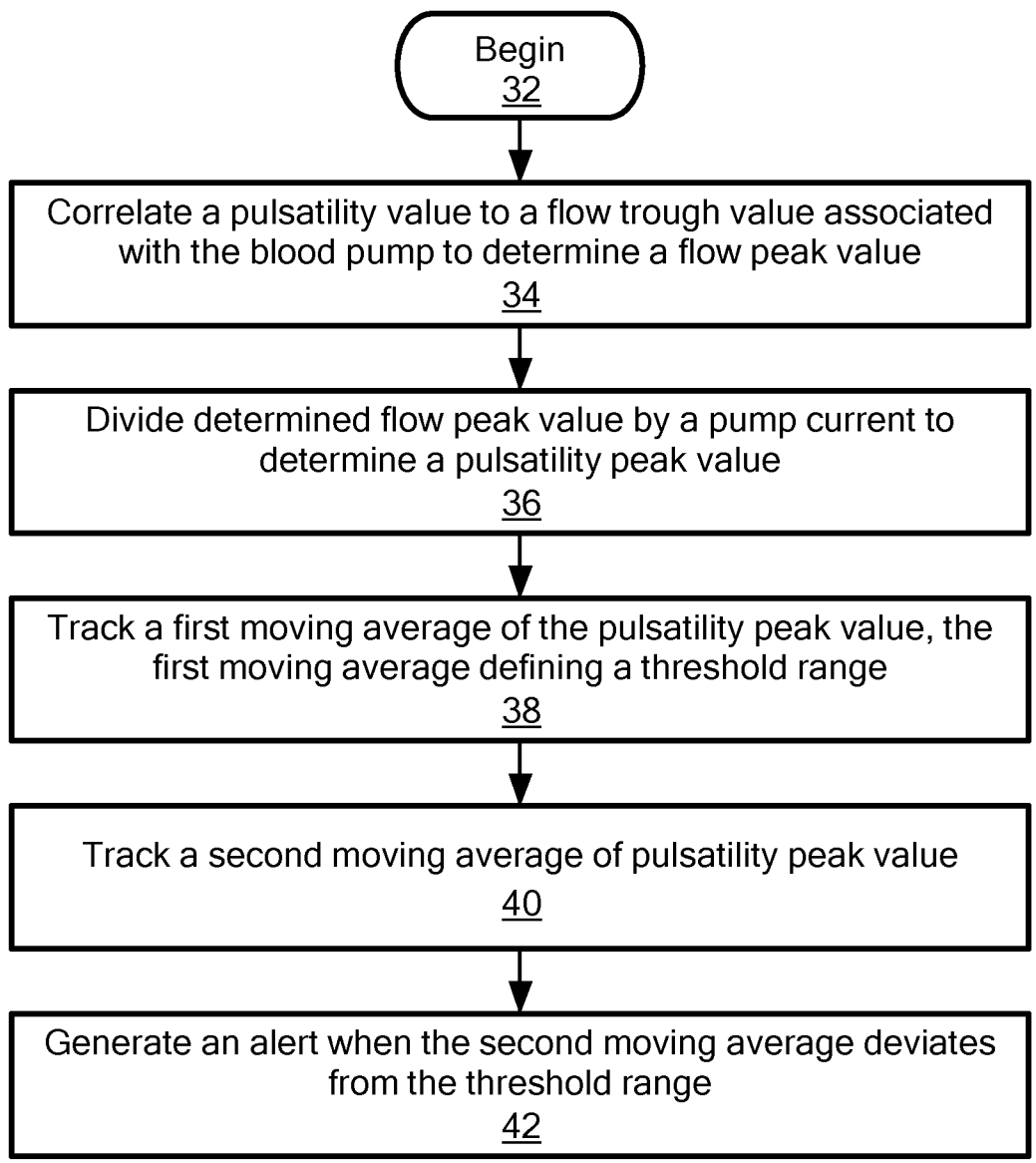
FIG. 2 is a flow diagram that illustrates a method of predicting an adverse event in a patient having the implantable blood pump of FIG. 1.

FIG. 2 is a flow chart of a method 30 of predicting an adverse event in a patient having an implantable blood pump, such as the blood pump 12, which is implemented by the system 10. The methods provided herein may include additional steps, omit one or more steps, and/or may be provided in an order which differs from that which is shown. Further, the methods may be applied to log file data, i.e., trends in patient parameters, and/or real-time waveforms. The method 30 determines a patient's flow pulsatility and provides retrospective review of patient information, beyond daily and cyclic changes, which may reveal meaningful and relatively severe changes in the flow pulsatility which correlate to the worsening of the patient's physiological state. Generally, the peak of a flow signal, i.e., a flow peak value, is used to trace the changes on the patient's flow signals despite the presence of events such as suction, which are otherwise known to disturb flow trough and pulsatility values. In addition, a pulsatility peak value is determined using the flow peak value divided by the pump current to normalize the flow signal to the patient's running speed and power conditions.

In one configuration, the method begins at step 32 in which the system 10 repeatedly or continuously determines the pulsatility value and the flow trough value. In step 34 the method 30 includes the system 10 correlating the pulsatility value to the flow trough value determine the flow peak value. For example, the pulsatility value is added to the flow trough value. In step 36, the determined flow peak value is divided by the pump current to determine the pulsatility peak value. In order to assist in quantifying the pulsatility peak value, in step 38, the system 10 proceeds to tracking a first moving average of the pulsatility peak value, and a corresponding standard deviation, which define a threshold range used to detect the onset of the adverse event.

In step 40, the system 10 continues with tracking a second moving average of the pulsatility peak value, the second moving average being faster than the first moving average. In one configuration, the first moving average is a twenty-four-hour moving average and the second moving average is approximately a two-hour duration; however, other durations are within the scope of the method 30. In step 42, the method 30 includes the system 10 generating an alert when the second moving average deviates from the threshold range. The second moving average deviating from the threshold range and the corresponding alert indicate a notable change in the patient's pulsatility relative to a previous time period.

The alert may be audible, visual, vibratory, or the like, and may be transmitted in real-time to the controller 14 or a remote location for clinician review and/or provided in a report. One or more instances of the alert occurring over a time period may be recorded, and based on the alert occurrences, the system 10 may determine a risk factor associated with a predicted onset of the adverse event. For example, the risk factor may be a one to ten scale with the likelihood of the adverse event occurring increasing in from one to ten. The risk factor may be used to classify changes in the patient's physiological state among a ranking system, such as a one to ten scale with ten being a relatively severe change in the patient's physiological state relative to a previous time period, signaling the need for immediate medical intervention.

Figure 3:
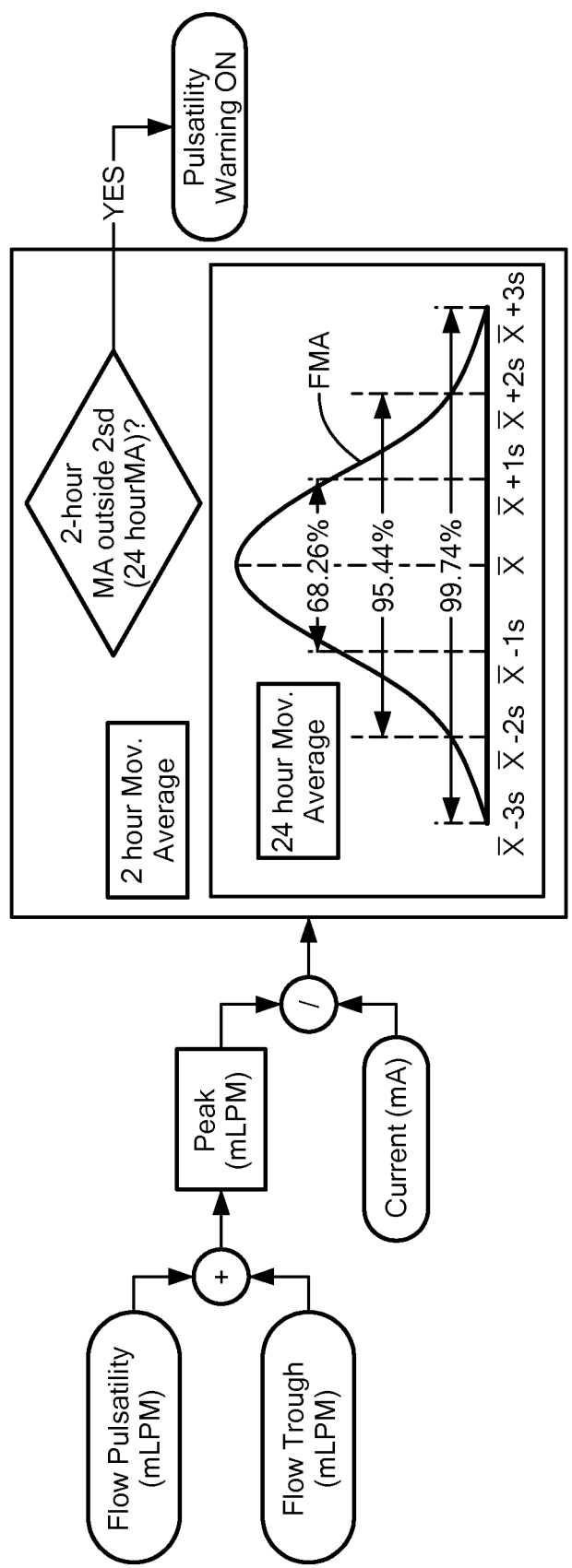
FIG. 3 is a block diagram the method of FIG. 2.
Figure 4:
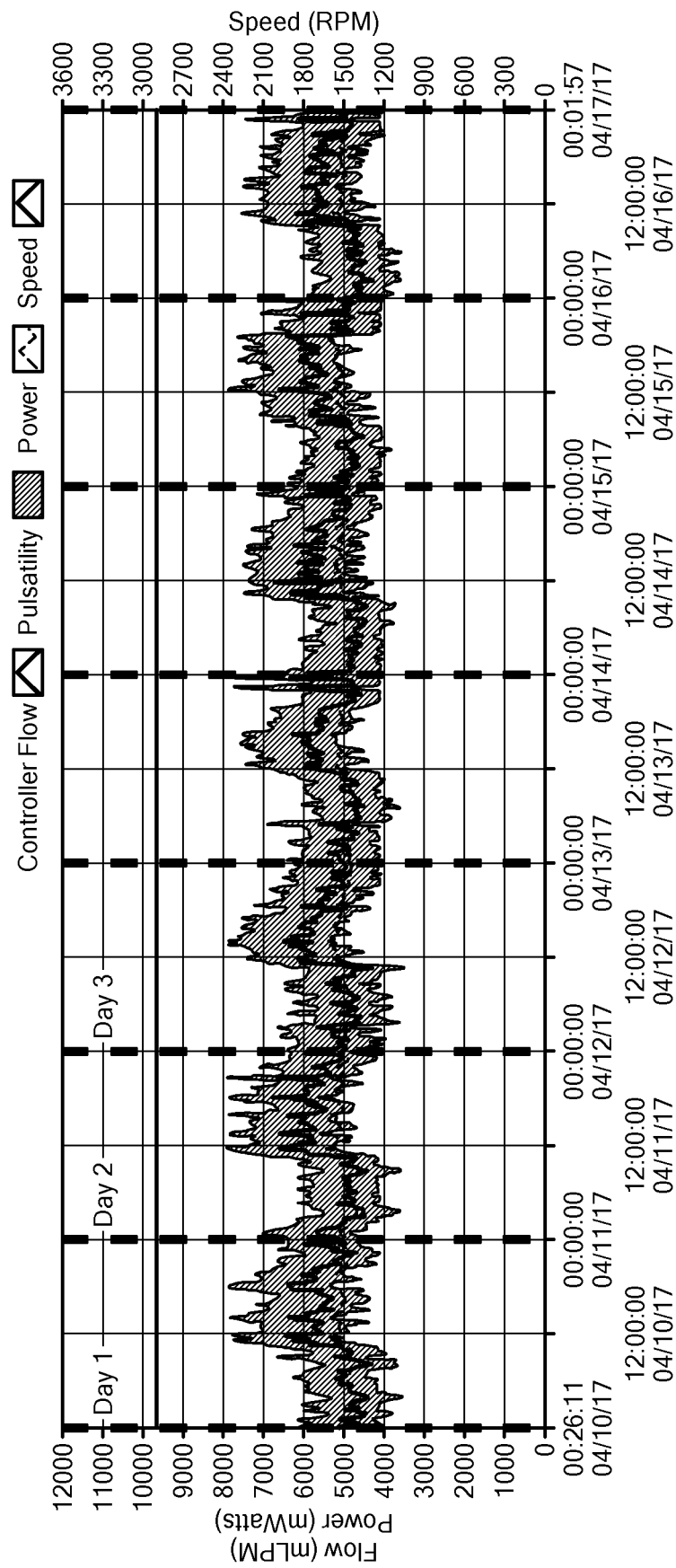
FIG. 4 is a graph that illustrates daily and cyclic changes in parameters including a flow value, pulsatility value, current value, and pump speed associated with the blood pump of FIG. 1 during use in the absence of an onset of the adverse event.
Figure 5:
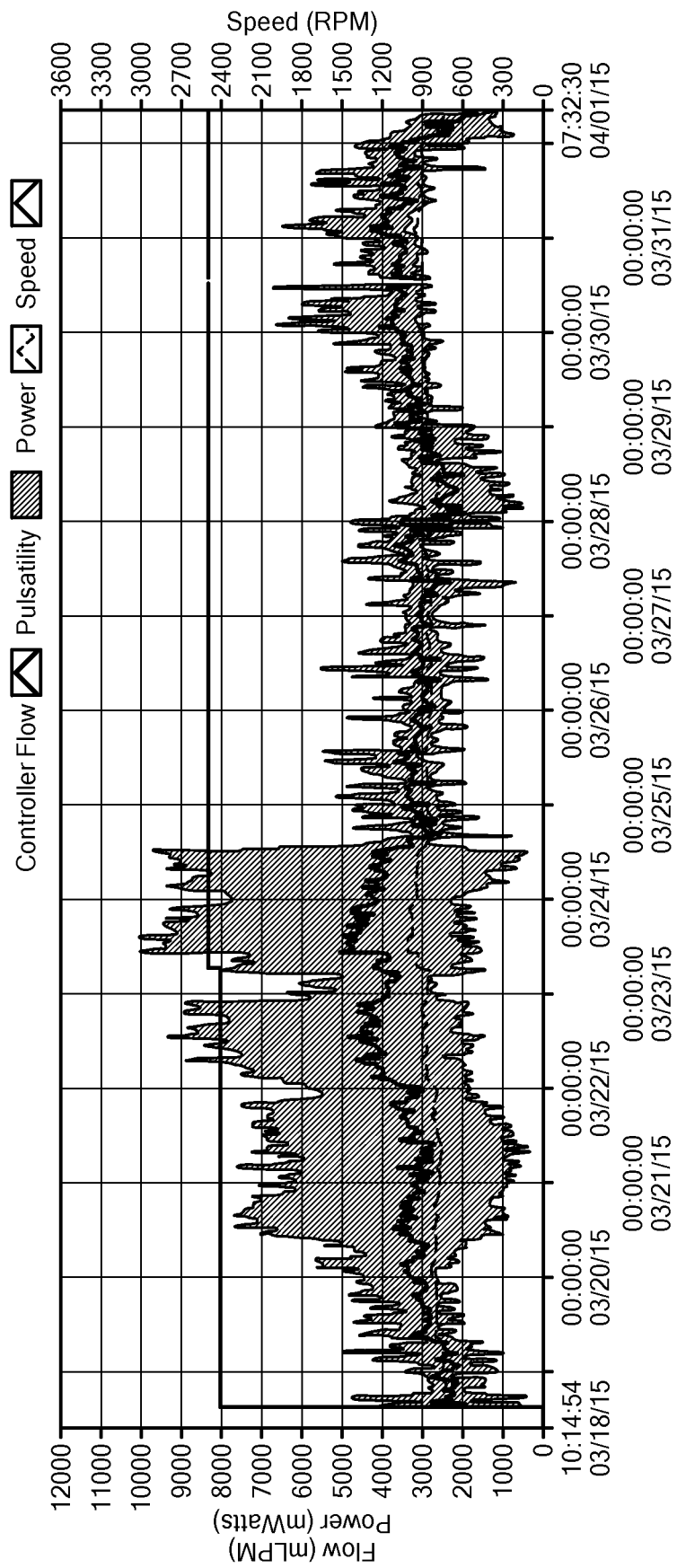
FIG. 5 is a graph that illustrates changes in the parameters of FIG. 4 during an adverse event.

FIG. 3 the method 30 executed as an algorithm including the first moving average is shown as a waveform "FMA". FIG. 4 is a graph depicting daily and cyclic changes in the flow value, pulsatility value, current value, and pump speed associated with the blood pump 12 during use in the absence of an onset of the adverse event. The graph is displayed as patient log files. FIG. 5 is a graph depicting changes the parameters of FIG. 4 during an adverse event. The changes in the pulsatility value are highlighted and analyzed through retrospective review to determine whether the patient's condition is worsening over time.

Figure 6:
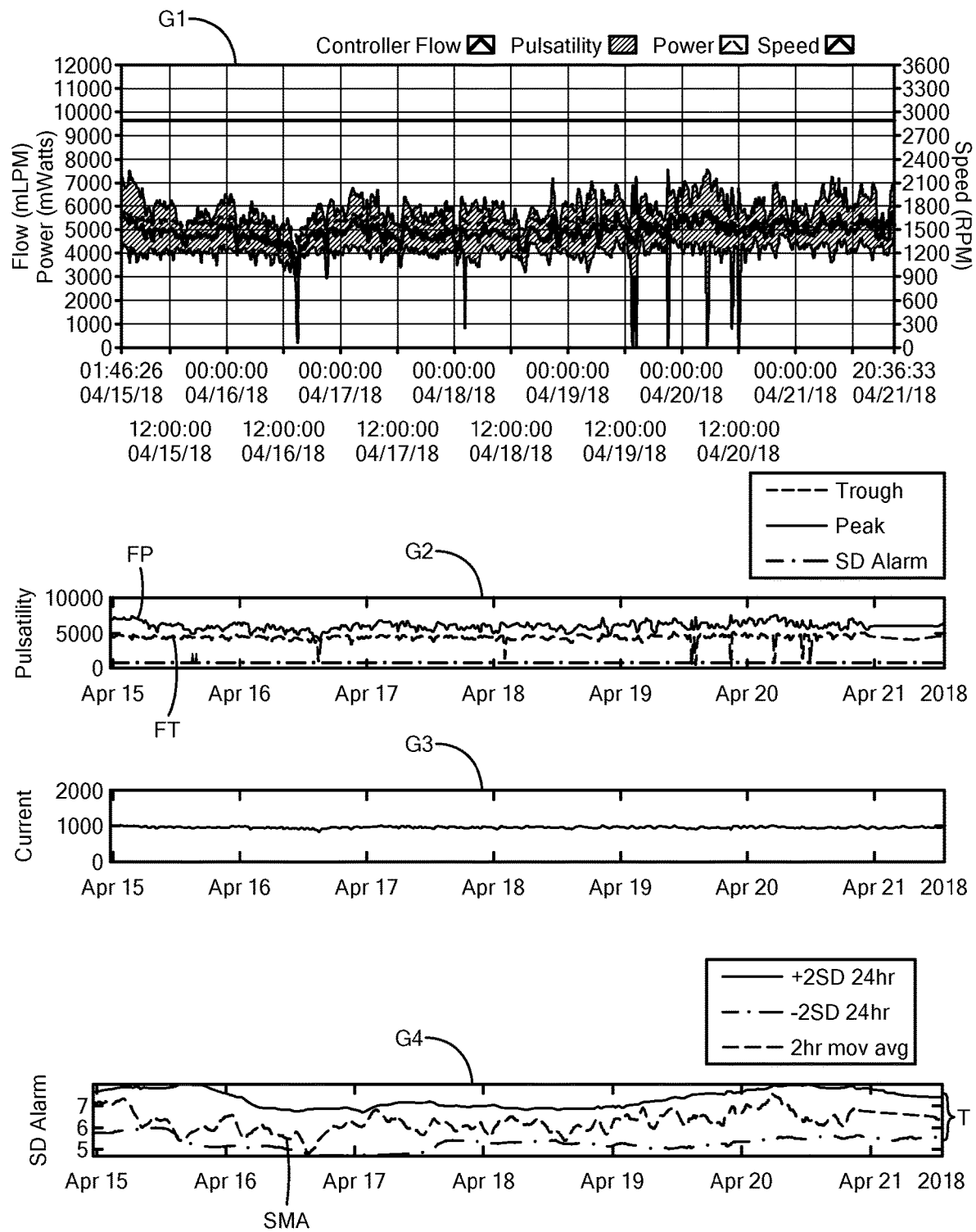
FIG. 6 is four graphs that illustrate changes in the parameters of FIG. 4.
Figure 7:
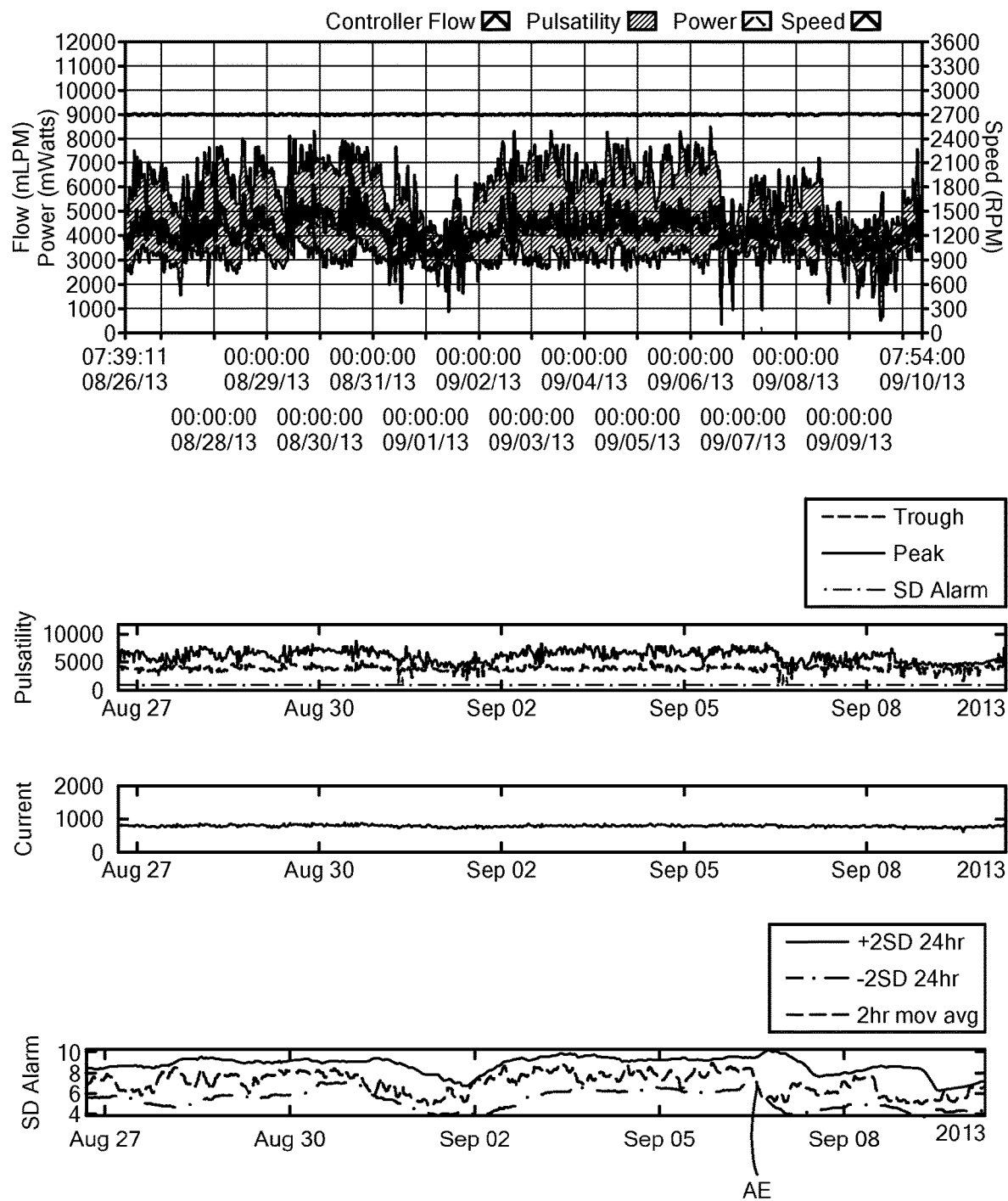
FIG. 7 is four graphs that illustrate the adverse event as right heart failure.

FIG. 6 depicts four graphs showing the system 10 continuously or repeatedly running to tracking the pulsatility peak value, such as through the algorithm. Graph "G1" depicts changes in the flow value, pulsatility value, current value, and pump speed associated with the blood pump 12. Graph "G2" depicts the flow peak value "FP" plotted relative to the flow trough value "FT" and graph "G3" depicts the current value. Graph "G4" depicts the threshold range "T" defined by the first moving average and the associated standard deviation. The second moving average "SMA" is plotted relative to the threshold range and a deviation from the threshold range indicates the notable change which prompts the alert. The deviation may be above or below the threshold range. In other words, the notable change is indicated when the second moving average crosses over the threshold range, whether above or below. The deviation amount and/or frequency may be used to quantify changes in the patient's homeostasis and/or hemodynamics which may be used as a risk factor or indicator of an onset of the adverse event. For example, FIG. 7 depicts 4 graphs including the parameters of FIG. 6 illustrating the adverse event as right heart failure. The deviation of the second moving average from the threshold range is designated as "AE".

Figure 8:
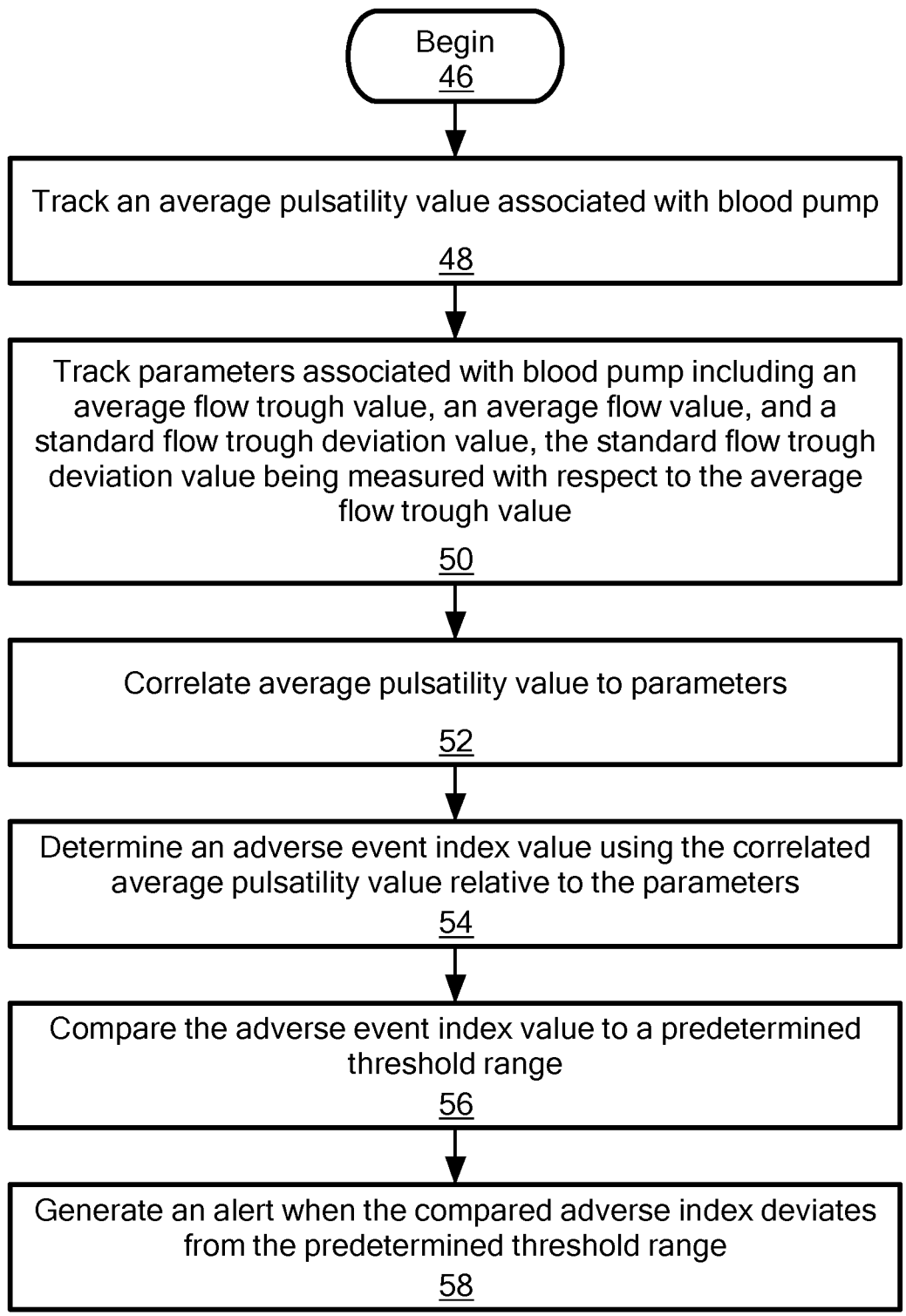
FIG. 8 is a flow chart that illustrates a method of predicting an adverse event in a patient having the blood pump of FIG. 1 which differs from the method of FIG. 2.

FIG. 8 is a flow chart of another method 44 of predicting an adverse event in a patient having the blood pump 12 which is implemented by the system 10. The method 44 provides retrospective review of patient information which may reveal that sustained periods of relatively high-pulsatility and low flow trough measured with respect to standard pulsatility and flow for the patient correspond to the deterioration of patient conditions and an onset of an adverse event. As such, the method 44 is configured to target sustained periods of relatively high-pulsatility and low flow trough values in individual patients.

In one configuration, the method 44 begins at step 46 and proceeds to step 48 including the system 10 tracking an average pulsatility value associated with the blood pump 12 during operation. The system 10 may operate in terms of an algorithm with the blood pump parameters being tracked over a duration expressed as a window size of days, week, or months. The average pulsatility value may be correlated to a scaling coefficient. In one example, the average pulsatility value is multiplied by the scaling coefficient of 100.

In step 50, the system 10 proceeds to tracking one or more parameters associated with the blood pump 12 including an average flow trough value, an average flow value, and a standard flow trough deviation value. The standard flow trough deviation value is measured with respect to the average flow trough value and is correlated to an offset value. The offset value is an added constant configured to prevent false identification of the periods of the high-pulsatility and low flow trough which may otherwise be affected by negative flow conditions absent the offset.

Figures 9, 10:
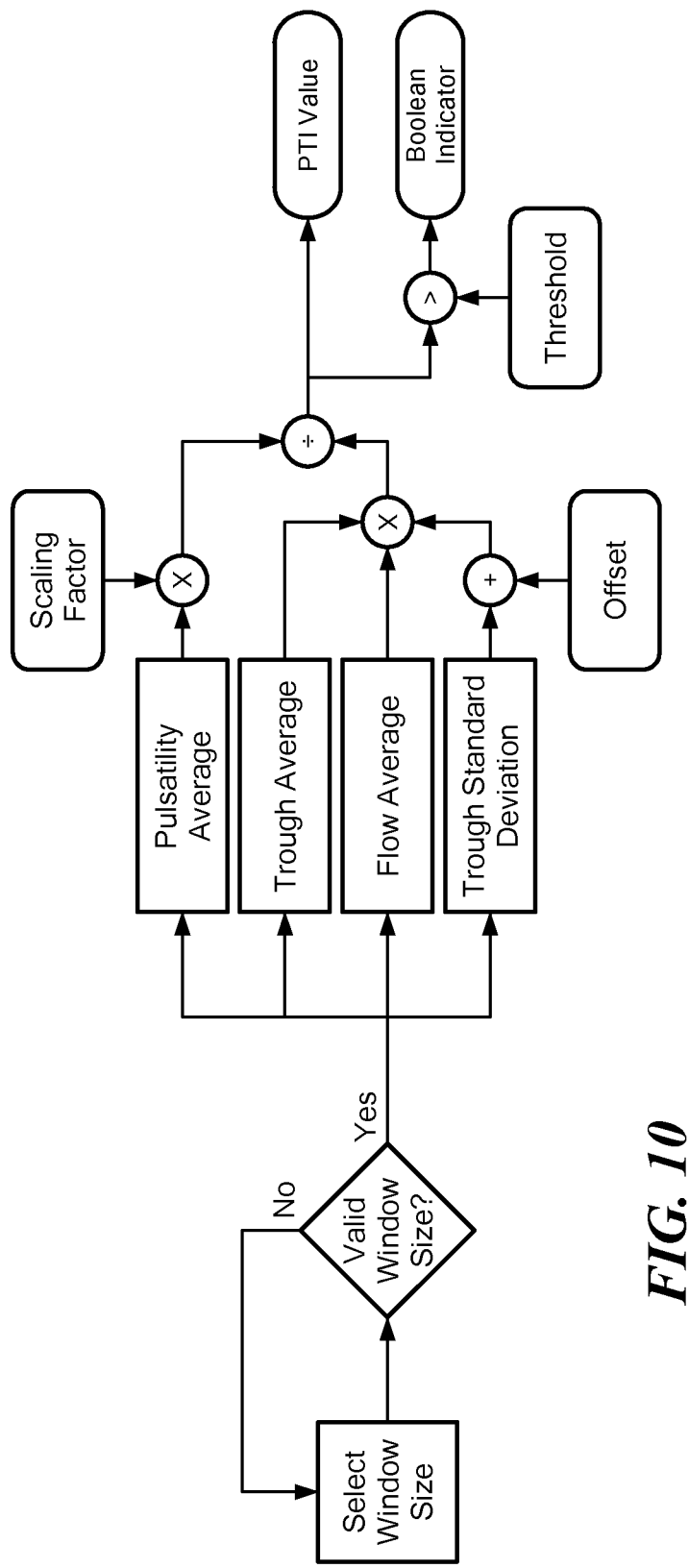
FIG. 9 is an equation that illustrates the method of FIG. 8.
FIG. 10 is a block diagram that illustrates the method of FIG. 8.

In step 52, the method 44 includes correlating the average pulsatility value to the parameters. For example, FIG. 9 depicts an equation including the average pulsatility value expressed as a numerator and the parameters being the average flow trough value added to the offset value and multiplied by the average flow value and the standard flow trough deviation value. In step 54, the method 44 includes determining an adverse event index value using the correlated average pulsatility value relative to the parameters. In other words, the equation is used to determine the adverse event index value which may be referred to as a pulsatility-trough indicator.

Proceeding to step 56, the method 44 compares the adverse event index value to a predetermined threshold range. In step 58, the system 10 generates an alert when the compared adverse event index value deviates from the predetermined threshold range. The alert includes the characteristics described above with respect to the method 30. The adverse event index value deviating from the predetermined threshold range indicates a presence of the adverse event, for example, a period of high-pulsatility and low flow trough. FIG. 10 is a block diagram depicting the method 44 used to determine the adverse event index value.

Figure 11:
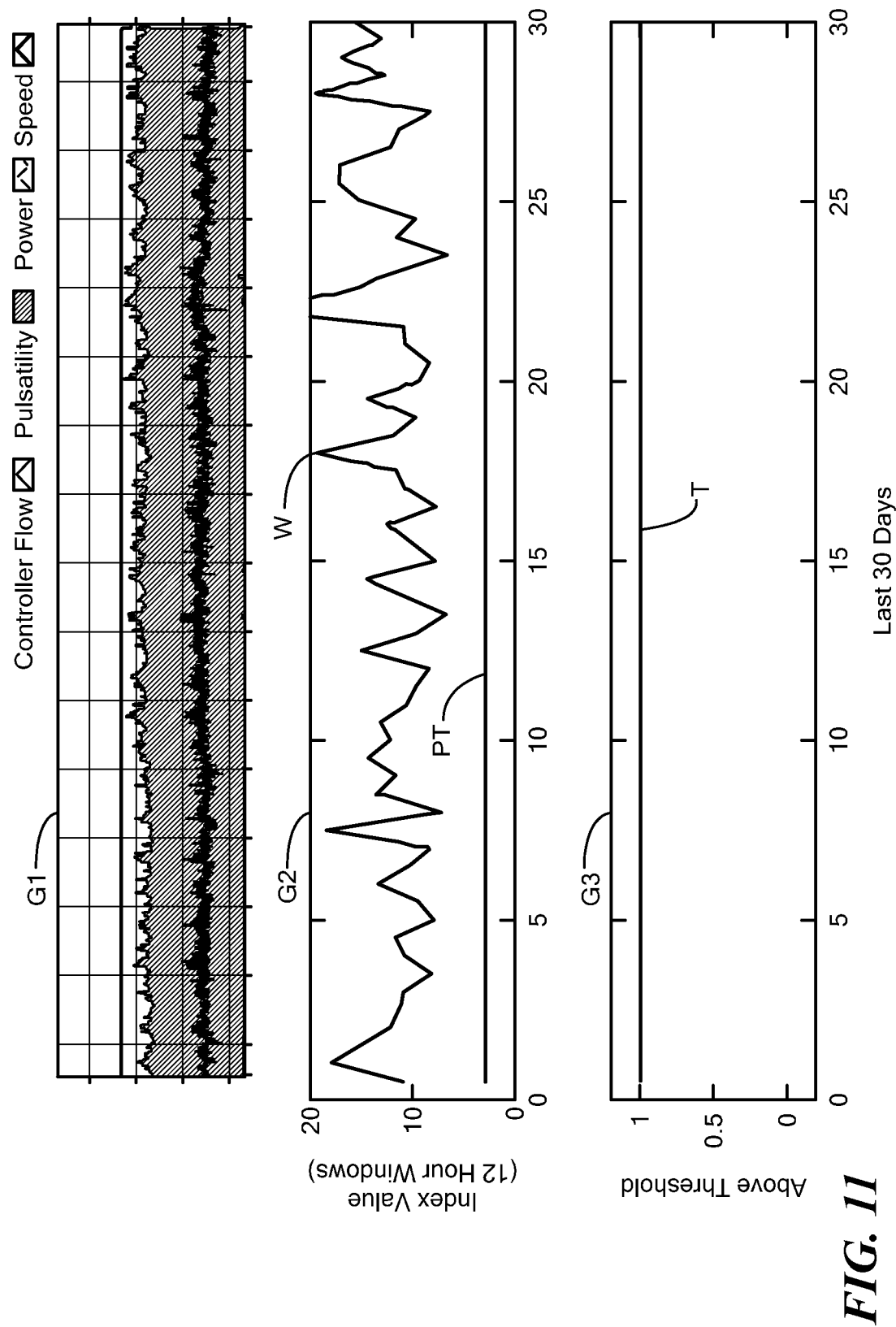
FIG. 11 is three graphs that illustrate an absence of an adverse event.

FIG. 11 is three graphs of sample data in the form of log file data. The graph "G1" depicts the average pulsatility value and the parameters associated with the blood pump expressed as waveforms. Graph "G2" depicts the adverse event index value expressed as a waveform "W" and predetermined threshold value "PT" over a twelve-hour window. The predetermined threshold "PT" is depicted as being below the waveform which indicates an absence of the tracked condition, i.e., the adverse event or period of high-pulsatility and low flow trough. The graph "G3" depicts the Boolean output "T" that indicates whether the index is greater than the predetermined threshold.

Figure 12:
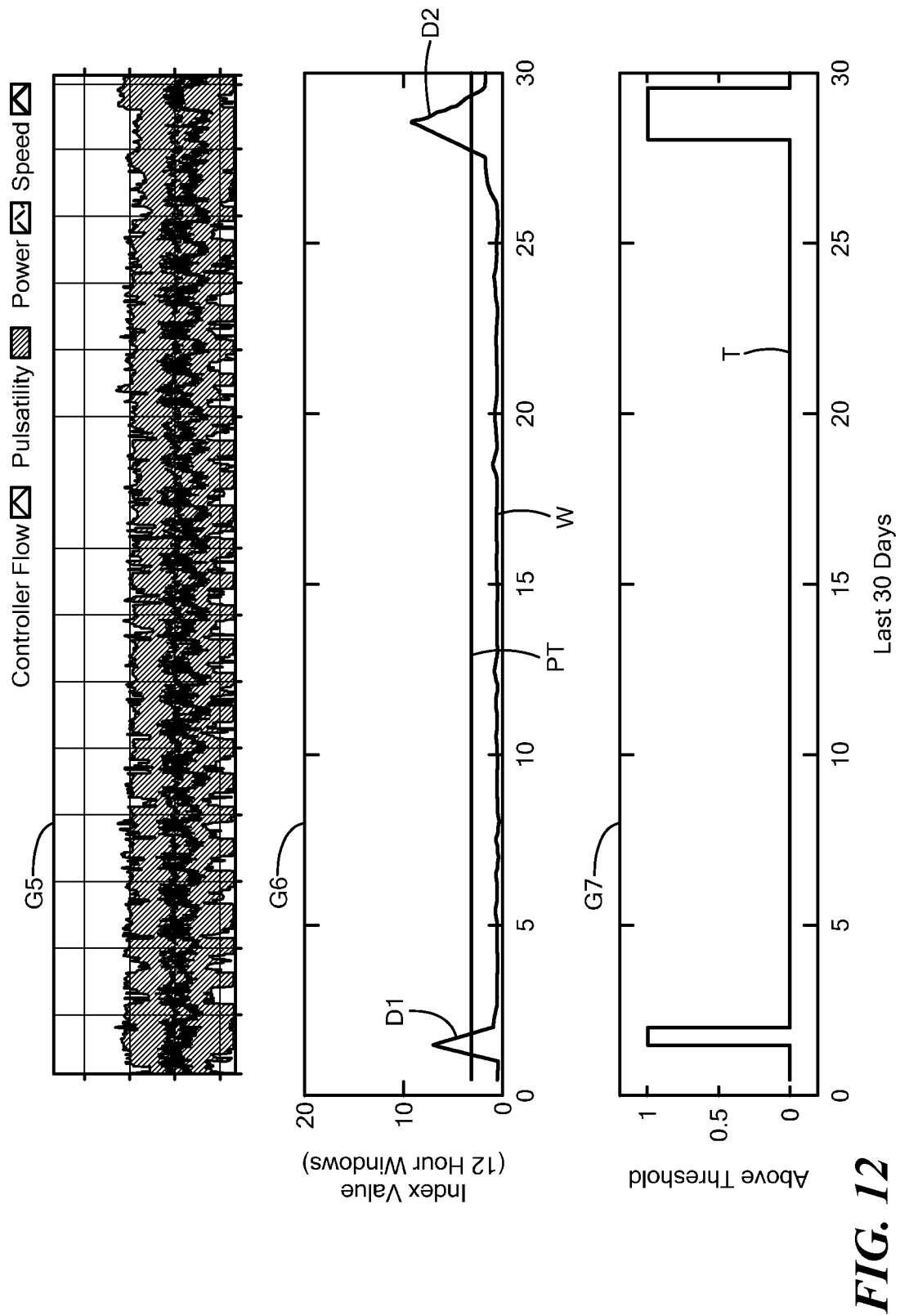
FIG. 12 is three graphs that illustrate the categories of information of FIG. 11 and the presence of the adverse event.

FIG. 12 is three graphs of sample data in the form of log file data displaying the categories of information shown in the graphs of FIG. 11 and designated as "G4", "G5", and "G6". The graph G4 provides the log file data of the parameters expressed as waveforms, whereas the graph G5 depicts the waveform over a twelve-hour window during which the waveform deviates from the predetermined threshold "PT" at the regions marked "D1" and "D2," which are indicative of the tracked condition. In particular FIG. 12 depicts the waveform crossing the predetermined threshold as indicative of the presence of the tracked condition. In other words, the adverse event index value exceeding the predetermined threshold range is expressed as an abnormal feature of the waveform. The graph "G6" depicts the Boolean output "T" that indicates whether the index is greater than the predetermined threshold.

The system 10 may be configured to determine one or more of the adverse event index values during one or more time periods, compare the adverse event index values to each other, and based on the compared adverse event index values, classify a patient's physiological state among a ranking system. The ranking system may be of various types, for example the one to ten scale discussed above.

Figure 13:
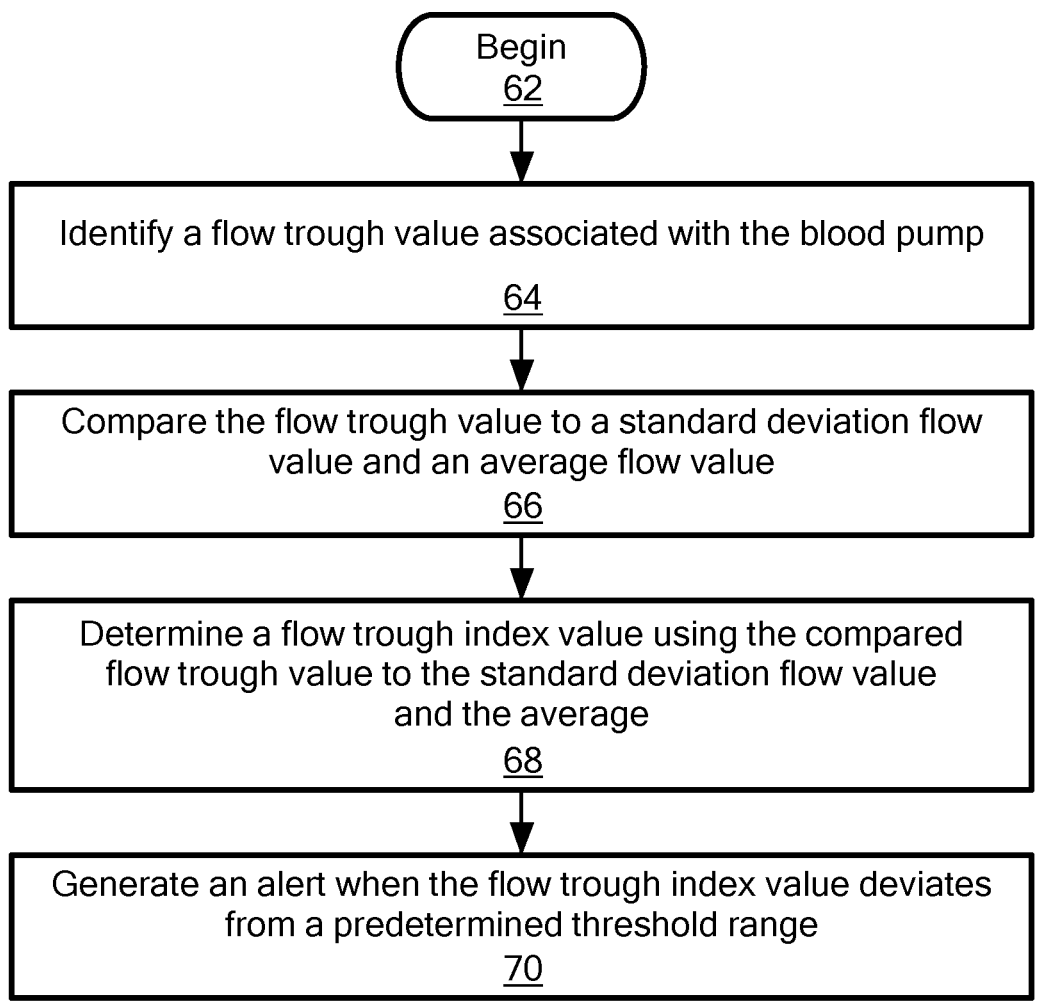
FIG. 13 is a flow chart that illustrates a method of predicting an adverse event in a patient having the blood pump which differs from the methods of FIGS. 2 and 8.

FIG. 13 is a flow chart of another method 60 of predicting an adverse event in a patient having the blood pump 12 which is implemented by the system 10. The adverse event may be a suction event characterized by relatively sharp negative deflections in estimated flow and power through the blood pump 12 relative to a patient's standard state. The method 60 provides retrospective review of patient information which may reveal meaningful and relatively severe changes in a patient's flow, e.g., flow trough, corresponding to suction events. Such changes can be quantified to assess conditions surrounding low flow and a suction burden. Generally, the method 60 includes determining a flow trough index value for more than one log file data points by taking the ratio of a standard deviation of a trough value to an average of the trough value.

In one configuration, the method 60 begins at step 62 and proceeds to step 64 including the system 10 identifying a flow trough value associated with the blood pump 12 during use. The flow trough value may be a minimum flow value relative to other flow values obtained during a select duration or window of blood flow through the blood pump 12 during use. In step 66, the method 60 includes comparing the flow trough value to a standard deviation flow value and an average flow value also determined during the duration. In step 68, the system 10 determines a flow trough index value using the compared flow trough value to the standard deviation flow value and the average flow value. In particular, the standard deviation flow value is divided by the average flow value to determine the flow trough index value. In step 70, the system 10 generates an alert when the flow trough index value deviates from a predetermined threshold range which indicates a presence of a suction condition. The alert may include the characteristics provided above with respect to the method 30. The predetermined threshold may be customized by a clinician based on how aggressively the clinician intends to track and assess the adverse event, such as the suction conditions.

Figure 14:
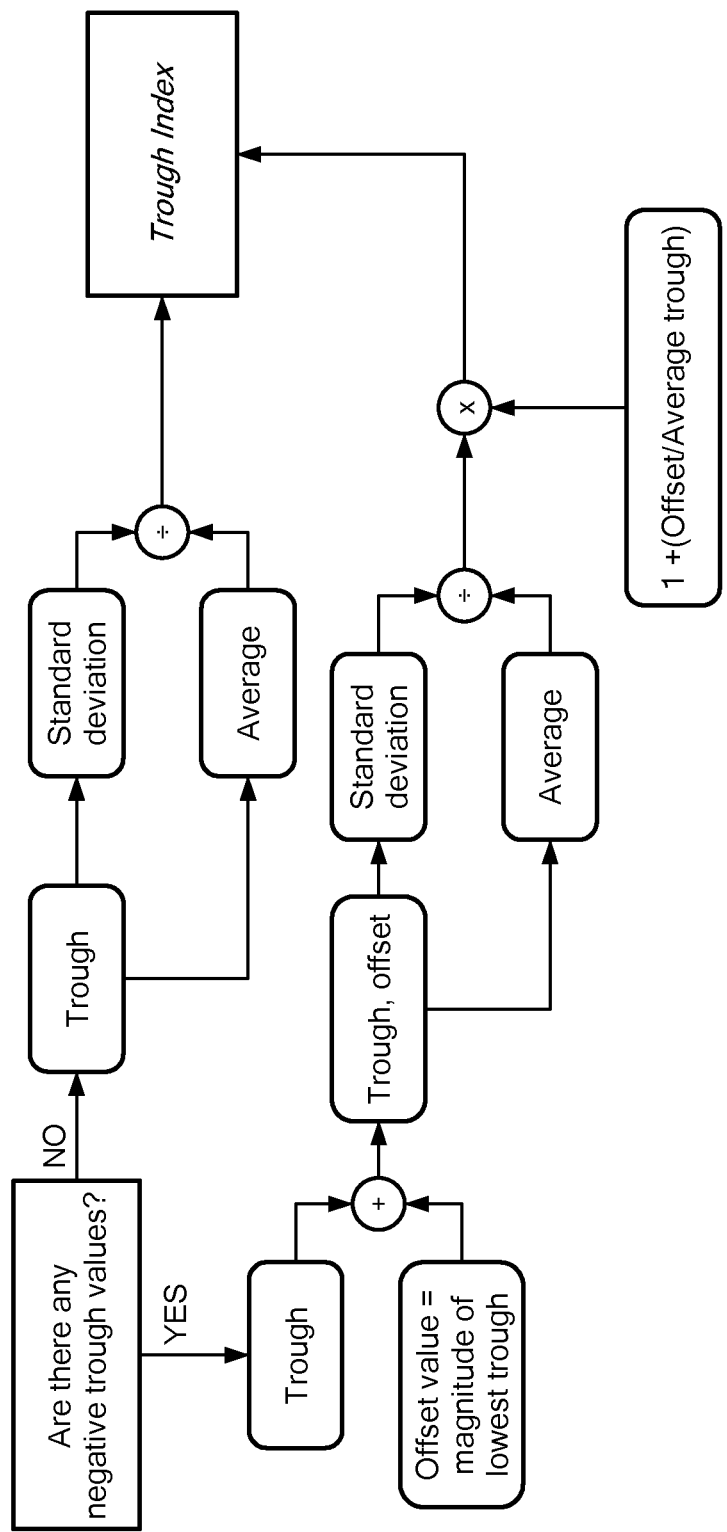
FIG. 14 is a block diagram that illustrates the method of FIG. 13 used to determine a flow trough index value.

FIG. 14 is a block diagram depicting the method 60 used to determine the flow trough index value. As depicted, prior to determining the flow trough value, the system 10 is configured to determine a presence of a negative flow trough value relative to a flow scale. The flow scale may be a select flow threshold for the particular patient. When the negative flow trough value is present, the flow trough value is correlated to a constant which is an offset value equal to a magnitude of a lowest trough value. In other words, the flow trough value is offset by the constant. The flow trough value which has been offset is correlated to the standard deviation flow value and the average flow value to determine the flow trough index value. Thereafter, the flow trough index value is multiplied by a constant, e.g., an offset value or corrective factor.

The flow trough index value may be used to quantify a suction prevalence associated with the blood pump 12. For example, the system 10 may be configured to determine more than one flow trough index value, and based on the flow trough index values which have been determined, quantify a suction prevalence associated with the blood pump. The suction prevalence is a predicted frequency or likelihood of the patient to experience a suction condition and may be used to classify a patient's physiological state among a ranking system. The ranking system may indicate a worsening of the patient's condition, as discussed above.

Figure 15:
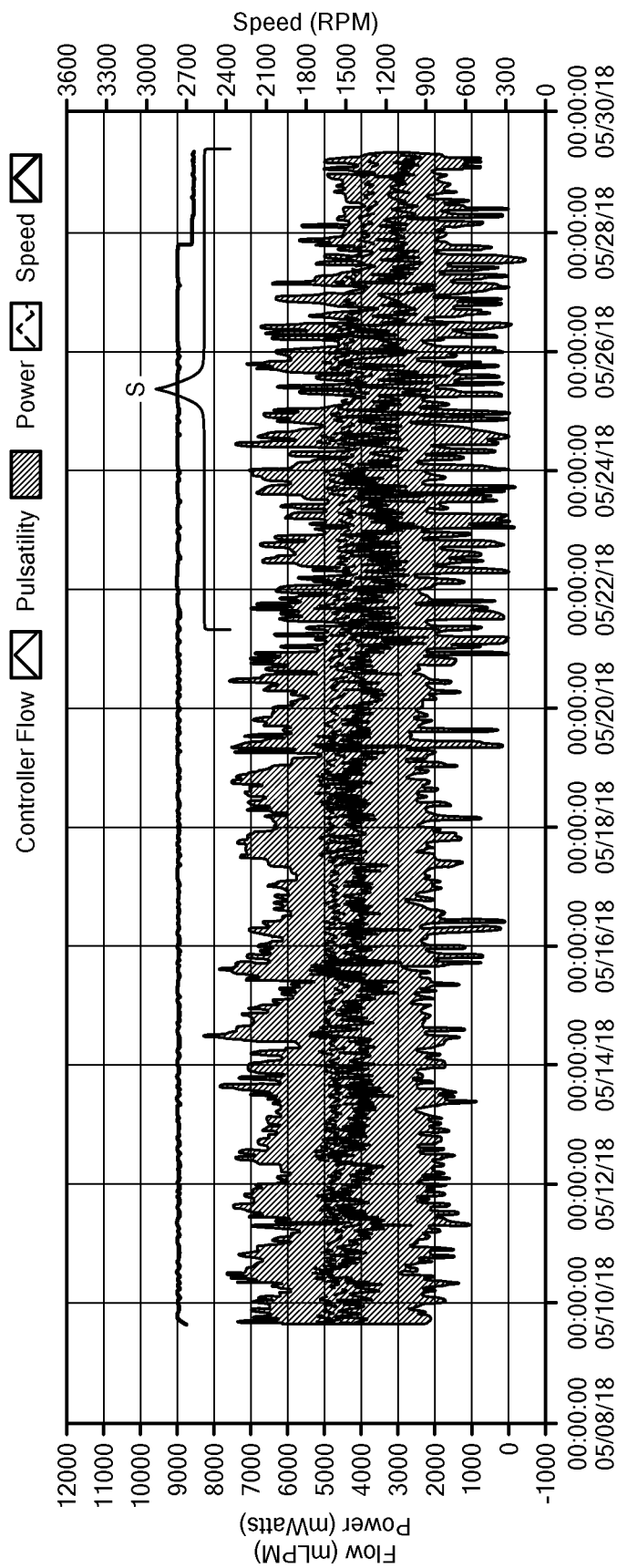
FIG. 15 is a graph that illustrates a presence of a suction condition.
Figure 16:
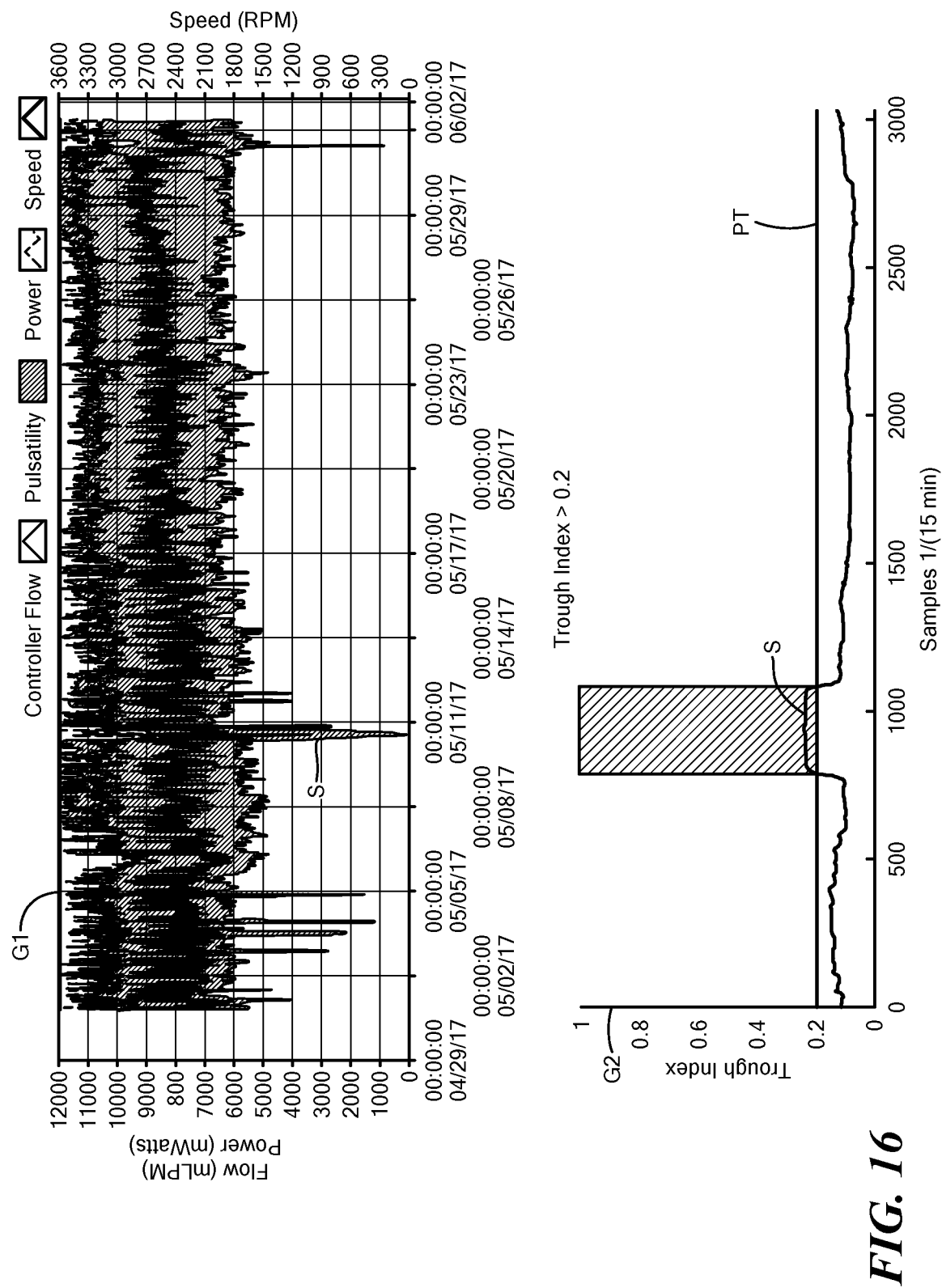
FIG. 16 is two graphs that illustrate the presence of a suction condition and a determined flow trough index value exceeding a predetermined threshold range.

FIG. 15 is a graph depicting changes in the flow value, pulsatility value, current value, and pump speed associated with the blood pump 12 during a suction condition at region "S" determined by the method 66. FIG. 16 is a graph "G1" of exemplary log file data including the flow value, pulsatility value, current value, and pump speed associated with the blood pump 12. The flow value and the pulsatility value deviate from the predetermined threshold at region "S". The graph "G2" corresponds to the graph G1 and depicts an exemplary trough index value determined using the method 66 and shown as an output which exceeds the predetermined threshold range "PT" at region S.

Figure 17:
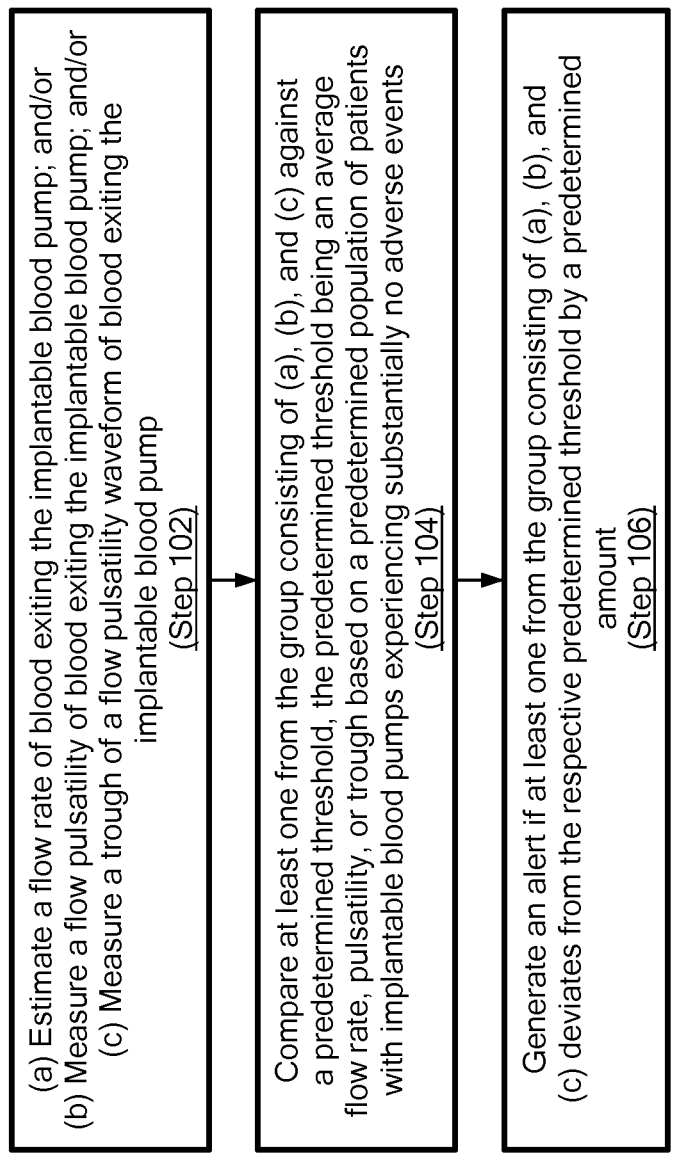
FIG. 17 is a flow chart of an exemplary method of predicting adverse events in patients with implantable blood pumps based on population data.

Referring now to FIG. 17, in which a method of predicting an adverse event in a patent having implantable blood pump 12 is shown. In these embodiments, the population data of patients who have pump 12 implanted during clinical trials is the basis for the thresholds described herein. In one configuration, the patients all have the same model implantable blood pump 12, for example, the HVAD pump. The method includes (a) estimating a flow rate of blood exiting the implantable blood pump 12, and/or (b) measuring a flow pulsatility of blood exiting the implantable blood pump 12, and/or (c) measuring a trough of a flow pulsatility waveform of blood exiting the implantable blood pump 12 (Step 102). The estimation or measurement of (a), (b), and/or (c) may be done in real-time or may be measured or estimated from log-files. At least one from the group consisting of (a), (b), and (c) may be compared against a predetermined threshold, the predetermined threshold being an average flow rate, pulsatility, and/or trough based on a predetermined population of patients with implantable blood pumps 12 experiencing substantially no adverse events (Step 104). An alert is generated if at least one from the group consisting of (a), (b), and (c) deviates from the respective predetermined threshold by a predetermined amount (Step 106). In another configuration, a set-speed of the pump 12 may be modified to increase or decrease the speed of the pump 12 if at least one from the group consisting of (a), (b), and (c) deviates from the respective predetermined threshold by a predetermined amount. For example, if suction is detected, the set-speed of the pump 12 may be reduced.

Figure 18:
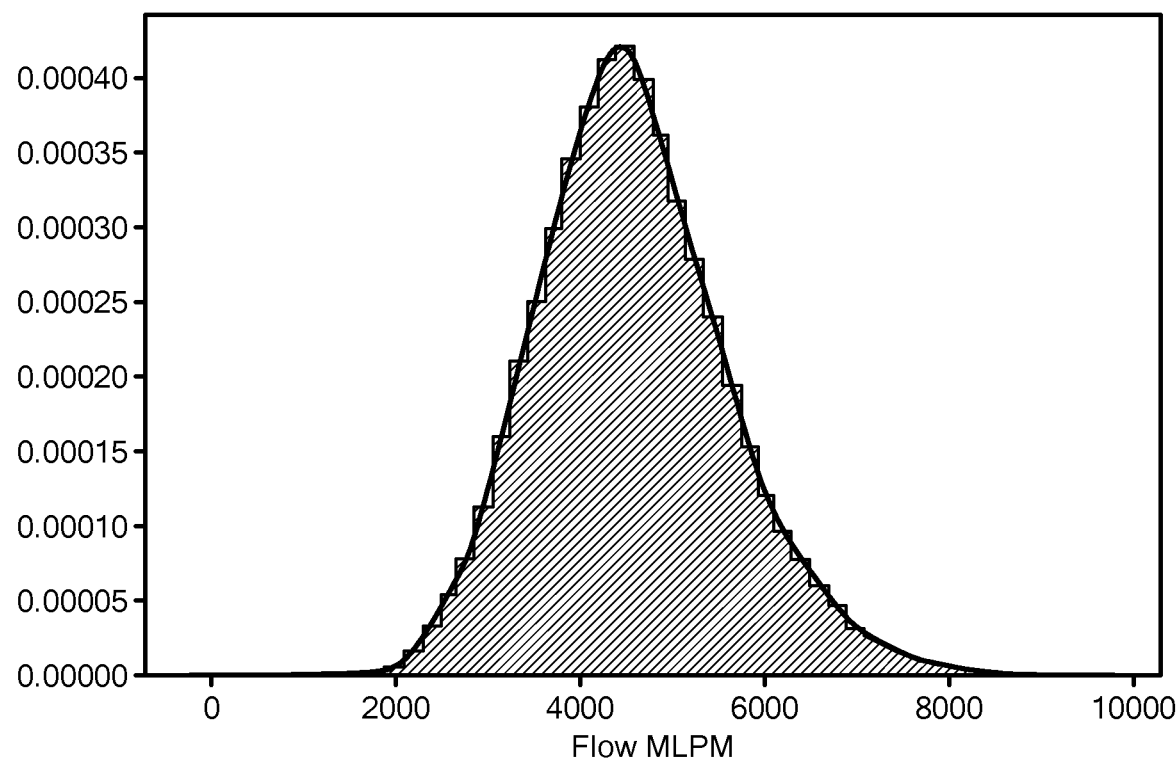
FIG. 18 is a graph showing an estimated flow rate for a predetermined population and its associated frequency.
Figure 19:
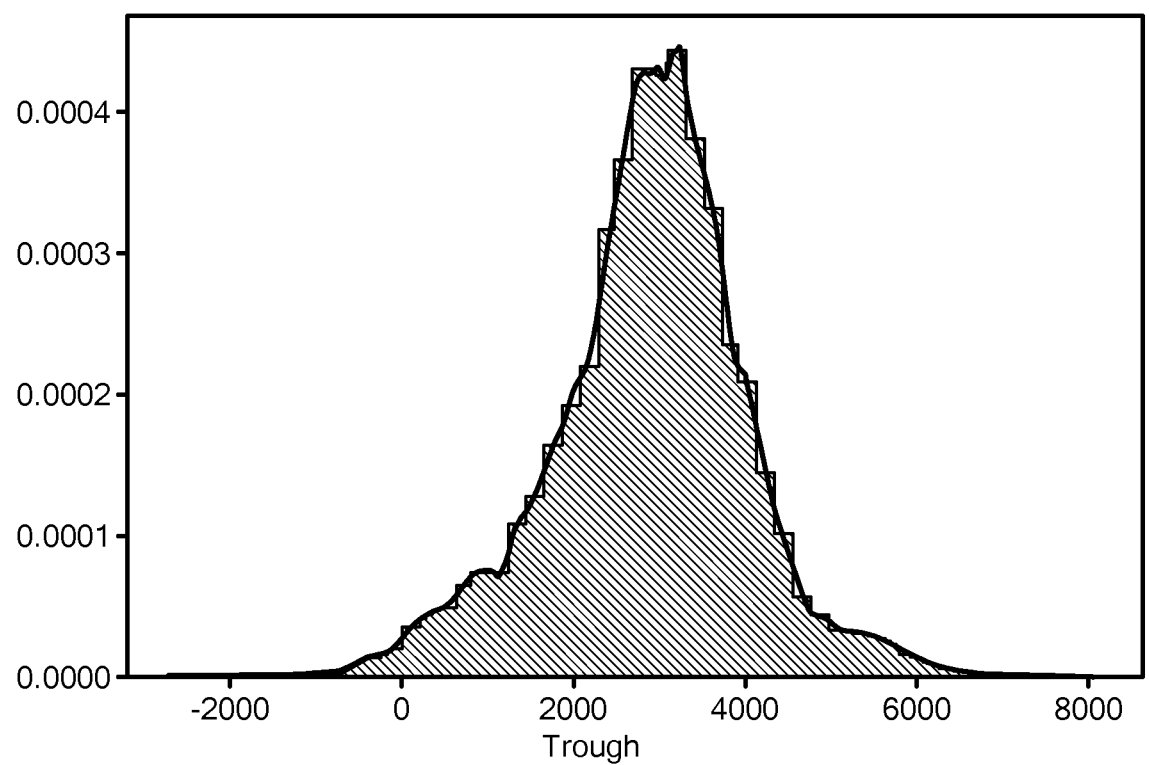
FIG. 19 is a graph showing the measured flow trough of flow pulsatility for a predetermined population and its associated frequency.
Figure 20:
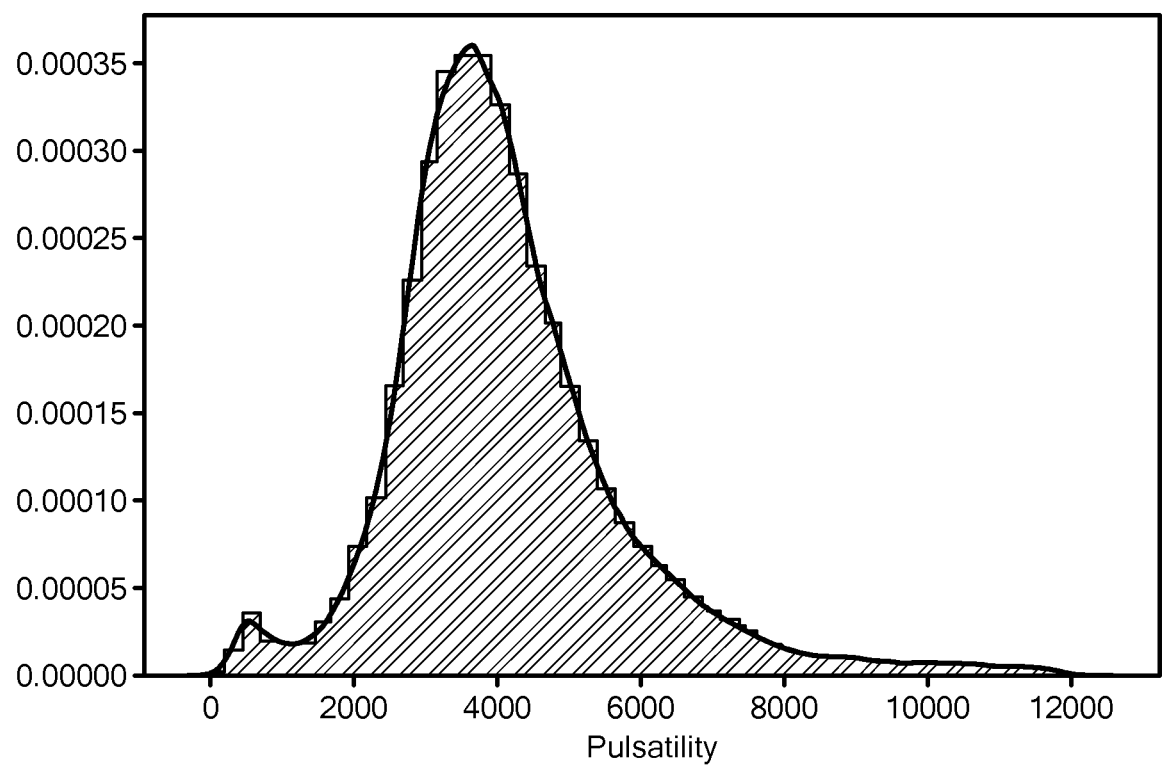
FIG. 20 is a graph showing the measured flow pulsatility for a predetermined population and its associated frequency.
Figure 21:
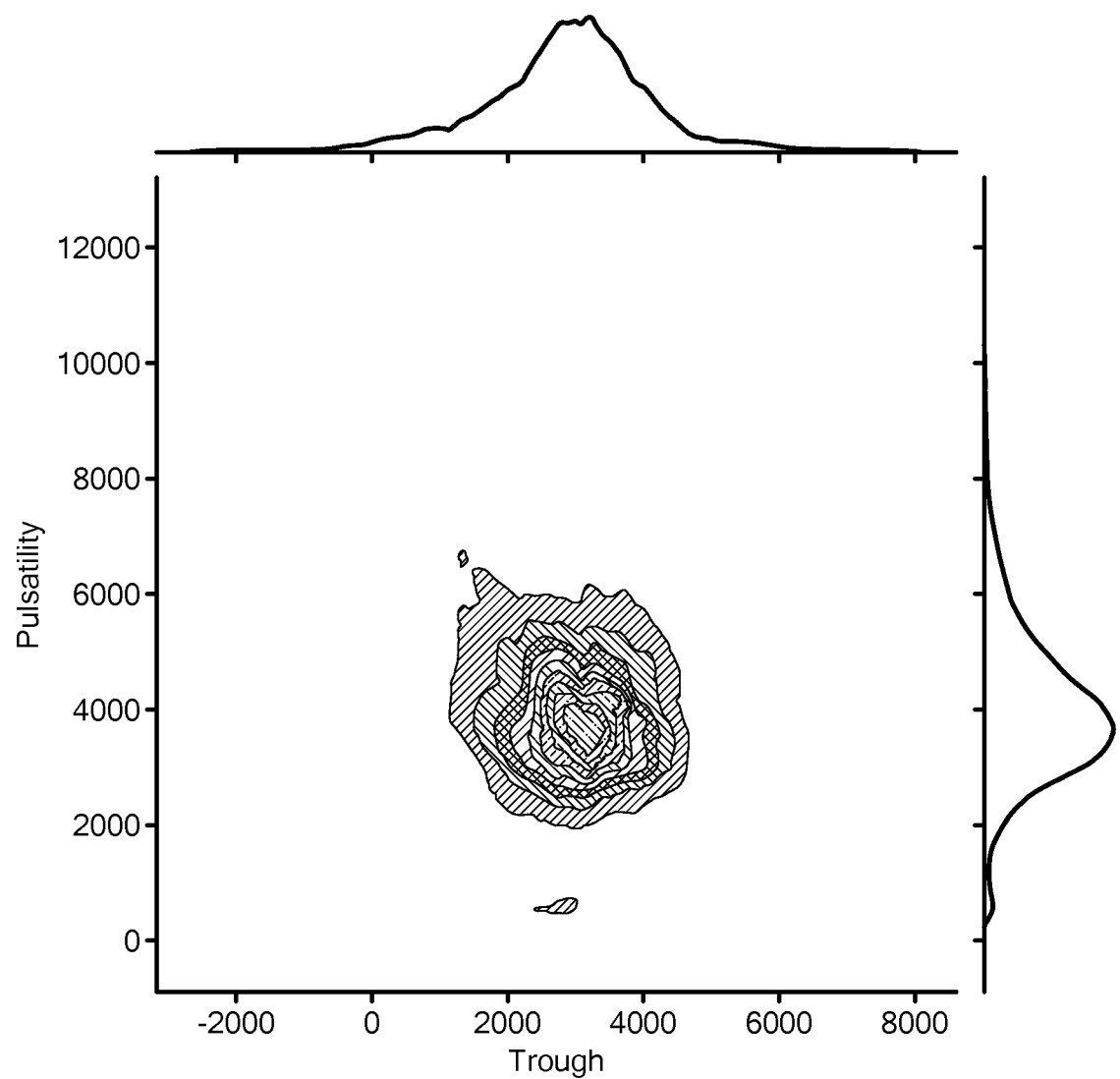
FIG. 21 is a density plot showing flow pulsatility versus flow trough.
Figure 22:
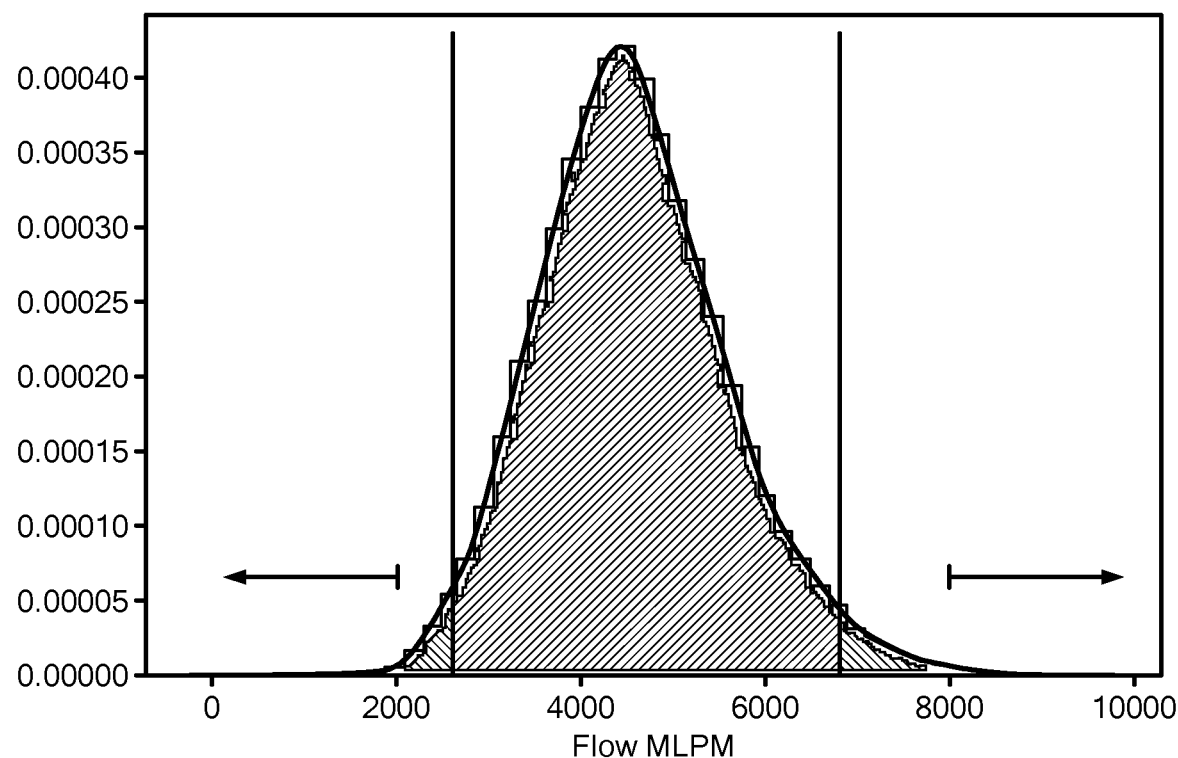
FIG. 22 is s a graph showing the estimated flow rate for a predetermined population and associated risk zones.
Figure 23:
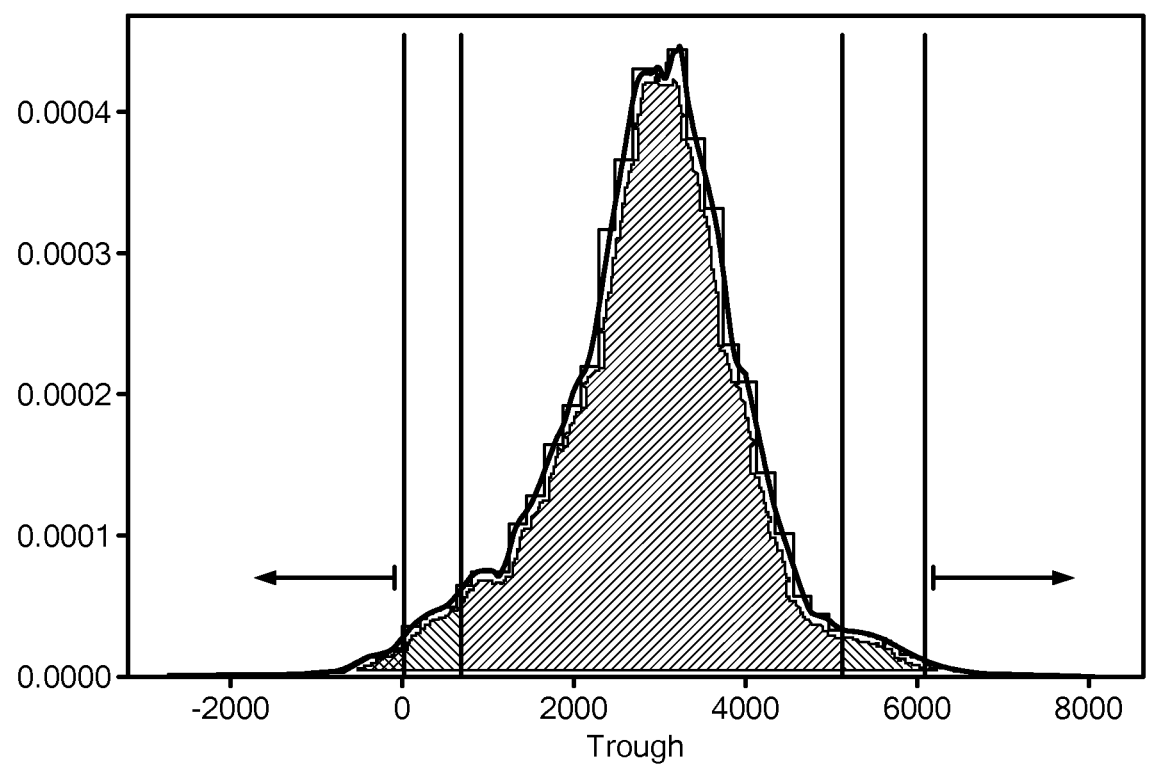
FIG. 23 is s a graph showing the measured flow trough of flow pulsatility for a predetermined population and associated risk zones.
Figure 24:
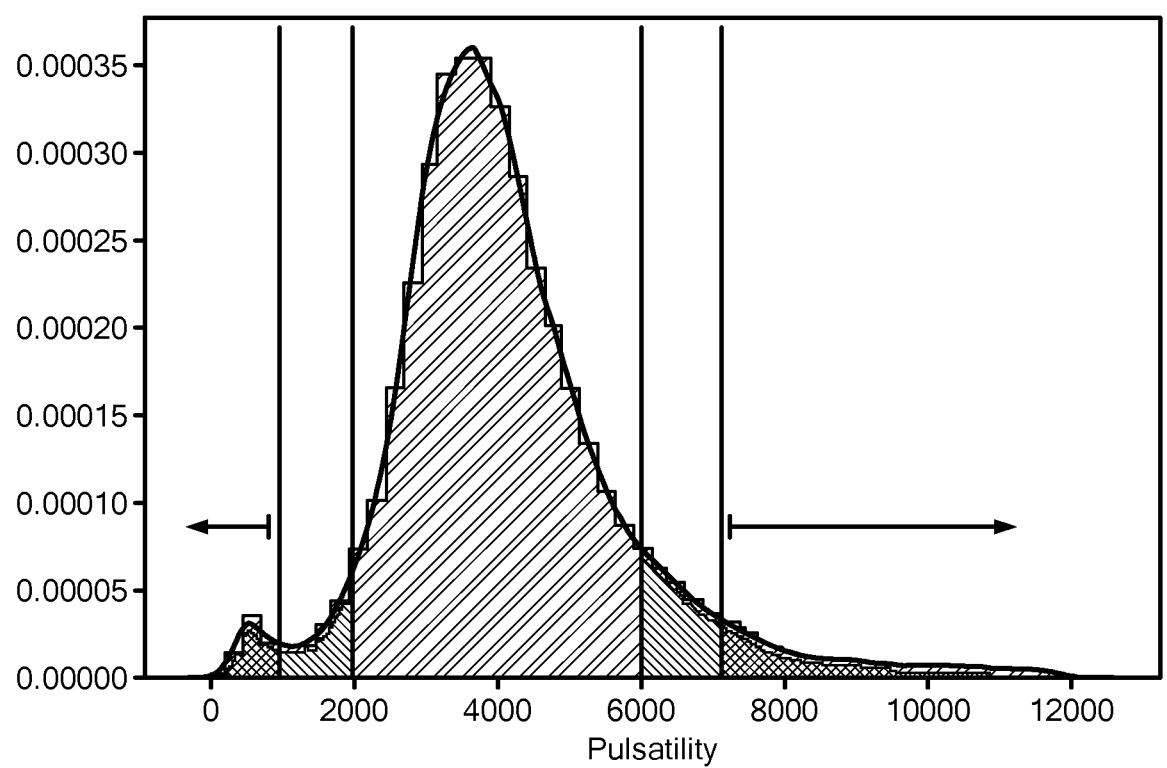
FIG. 24 is a graph showing the measured flow pulsatility for a predetermined population and associated risk zones.

In one example, over 99% of the observations of the log-files of the patients with implantable blood pump 12 had no suction events. From those observations, population-based thresholds were determined. For example, the predetermined population depicted an average flow value of 4.582 LPM with a standard deviation of 1.017 LPM. A graph showing the estimated pump flow rate in mLPM is shown in FIG. 18. The flow trough of a flow pulsatility waveform was also measured to be an average of 2.903 LPM with a standard deviation of 1.115 LPM. A graph showing the measured flow trough of a flow pulsatility waveform in mLPM is shown in FIG. 19. The average flow pulsatility, peak-to-tough, was measured to be 4.127 LPM with a standard deviation of 1.561 LPM. A graph showing the measured flow pulsatility in mLPM is shown in FIG. 20. In one configuration, an alert is generated if one or more of (a), (b), and/or (c) deviates from the respective predetermined threshold by a predetermined amount. For example, based on the population data of patients in clinical trials, an operational point may be determined based on (a), (b), and/or (c). That is, as shown in FIG. 21, at a particular impeller speed of pump 12, when visualizing the density of the population data it is observed that most of the data points are centered around 4 LPM for pulsatility and around 3 LPM for trough flow. From this data it is observed that most of the data points fall between 2 LPM and 6 LPM and there are no negative flows indicating a lack of suction. Moreover, risk zones for flow, trough, and pulsatility may also be determined based on the population data based on a predetermined baseline of data, for example a 24-hour window over one week. For example, as shown in FIG. 22, in which estimated flow plus or minus one standard deviation is shown compared to its distribution of the population. The shaded area is indicative of suboptimal performance, i.e. outside of the range of 2 LPM to 6 LPM for pulsatility and trough flow, and if the estimated flow deviates by at least one standard deviation from the predetermined threshold flow, an alert may be generated either in the log-file or in real time. Alternatively, or additionally, as shown in FIG. 23 (flow trough) and FIG. 24 (pulsatility) may be plotted against its distribution of the population. In each case, deviation from a one standard deviation, in either the positive or negative, direction is indicative of suboptimal performance and deviation by two standard deviations, in either the positive or negative direction is indicative of an adverse event, for example suction.

Figure 25:
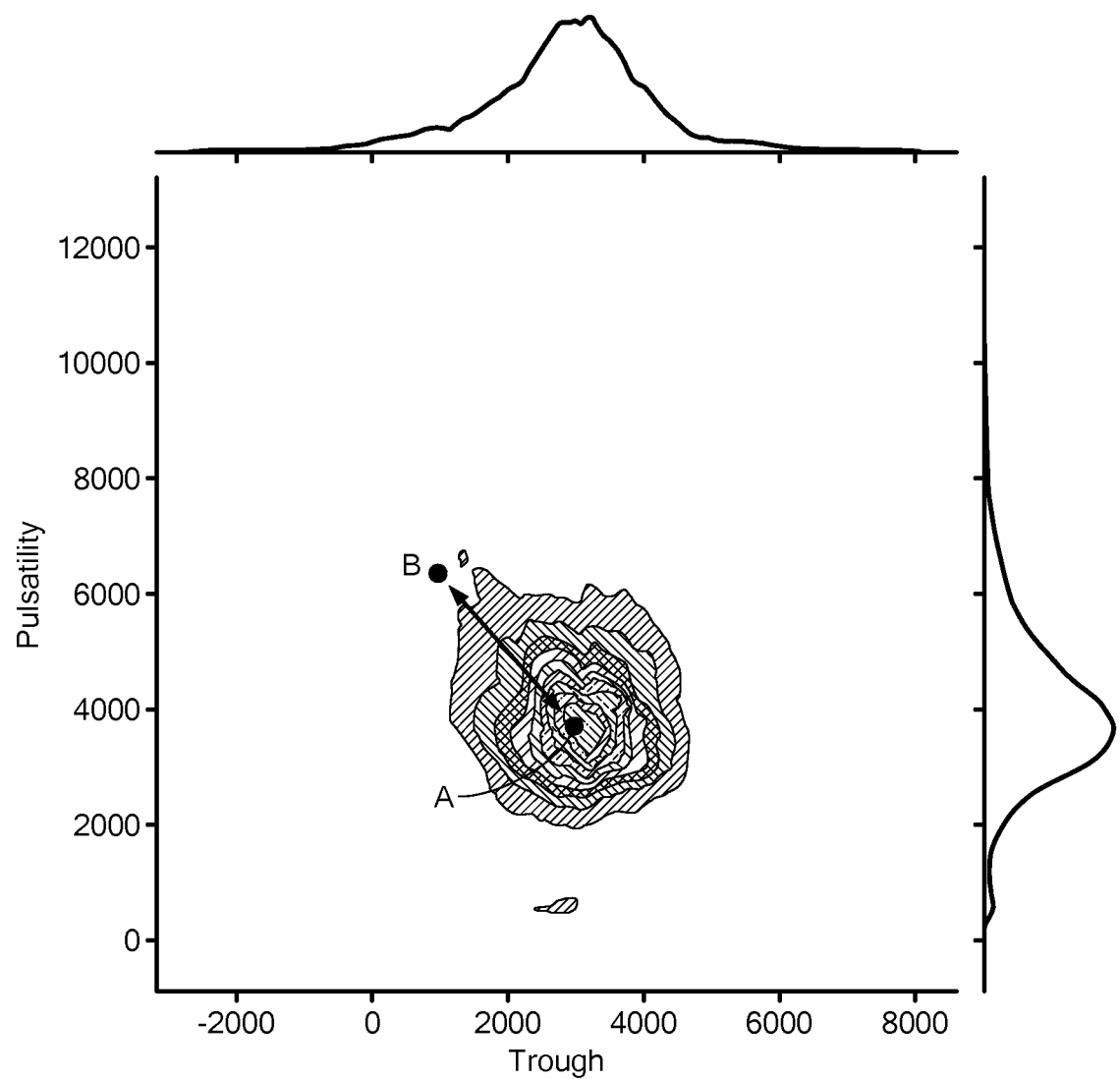
FIG. 25 a density plot showing flow pulsatility versus flow trough and a vector from point A to point B.

Moreover, in another example, as shown in FIG. 25, if the operating point should deviate by a predetermined amount in a predetermined direction away from the average flow, trough, or pulsatility, then an alert may be generated in real-time or in a log-file. For example, using vector analysis, if the magnitude and/or direction of a particular operating point should deviate from an average operating point, for example point A to point B, then an alert may be generated. That is, the change in direction and magnitude on a point-by-point basis may be calculated, and may be predictive of adverse event.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of predicting an adverse event in a patient having an implantable blood pump, comprising:
    at least one from the group consisting of:
        (a) estimating a flow rate of blood exiting the implantable blood pump;
        (b) measuring a flow pulsatility of blood exiting the implantable blood pump; and
        (c) measuring a trough of a flow pulsatility waveform of blood exiting the implantable blood pump;
    comparing the at least one from the group consisting of (a), (b), and (c) against a predetermined threshold, the predetermined threshold being an average flow rate, pulsatility, or trough based on a predetermined population of patients with implantable blood pumps experiencing substantially no adverse events; and
    generating an alert if at least one from the group consisting of (a), (b), and (c) deviates from the respective predetermined threshold by a predetermined amount.

2. The method of claim 1, wherein the predetermined amount is at least one standard deviation.

3. The method of claim 2, wherein the alert is indicative of sub-optimal performance.

4. The method of claim 1, wherein the predetermined amount is at least two standard deviations.

5. The method of claim 4, wherein the alert is indicative of an adverse event.

6. The method of claim 5, wherein the adverse event is suction.

7. The method of claim 1, wherein the implantable blood pump is a centrifugal blood pump.

8. The method of claim 1, wherein (a), (b), and (c) are recorded in a log-file, and wherein comparing the at least one from the group consisting of (a), (b), and (c) against the threshold includes comparing the recorded log-file against the predetermined threshold.

9. The method of claim 1, wherein (a), (b), and (c) are measured or estimated in real-time, and wherein comparing the at least one from the group consisting of (a), (b), and (c) against the threshold includes comparing the real-time estimation or measurement of (a), (b), and (c) against the predetermined threshold.

10. The method of claim 1, wherein the predetermined population of patients with implantable blood pumps experiencing substantially no adverse events each had implanted a same model implantable blood pump.

11. A system for predicting an adverse event in a patient having an implantable blood pump, comprising:
    a controller having processing circuitry in communication with the implantable blood pump and being configured to:
        at least one from the group consisting of:
            (a) estimate a flow rate of blood exiting the implantable blood pump;
            (b) measure a flow pulsatility of blood exiting the implantable blood pump; and
            (c) measure a trough of a flow pulsatility waveform of blood exiting the implantable blood pump;
        compare the at least one from the group consisting of (a), (b), and (c) against a predetermined threshold, the predetermined threshold being an average flow rate, pulsatility, or trough based on a predetermined population of patients with implantable blood pumps experiencing substantially no adverse events; and
        generate an alert if at least one from the group consisting of (a), (b), and (c) deviates from the respective predetermined threshold by a predetermined amount.

12. The system of claim 11, wherein the predetermined amount is at least one standard deviation.

13. The system of claim 12, wherein the alert is indicative of sub-optimal performance.

14. The system of claim 11, wherein the predetermined amount is least two standard deviations.

15. The system of claim 14, wherein the alert is indicative of an adverse event.

16. The system of claim 15, wherein the adverse event is suction.

17. The system of claim 11, wherein (a), (b), and (c) are recorded in a log-file, and wherein the controller being configured to compare the at least one from the group consisting of (a), (b), and (c) against the threshold includes the controller being configured to compare the recorded log-file against the predetermined threshold.

18. The system of claim 11, wherein (a), (b), and (c) are measured or estimated in real-time by the controller, and wherein the controller being configured to compare the at least one from the group consisting of (a), (b), and (c) against the threshold includes the controller being configured to compare the real-time estimation or measurement of (a), (b), and (c) against the predetermined threshold.

19. The system of claim 11, wherein the predetermined population of patients with implantable blood pumps experiencing substantially no adverse events each had implanted a same model implantable blood pump.

20. A system for predicting an adverse event in a patient having an implantable blood pump, comprising:

a controller having processing circuitry in communication with the implantable blood pump and being configured to:
(a) estimate a flow rate of blood exiting the implantable blood pump;
(b) measure a flow pulsatility of blood exiting the implantable blood pump; and
(c) measure a trough of a flow pulsatility waveform of blood exiting the implantable blood pump;
compare (a), (b), and (c) against a predetermined threshold, the predetermined threshold being an average flow rate, pulsatility, and trough based on a predetermined population of patients with a same model implantable blood pump experiencing substantially no adverse events; and
generate an alert if (a), (b), and (c) deviates from the predetermined threshold by at least one standard deviation, the alert being indicative of suction.

* * * * *